US012642674B2

(12) United States Patent
   Lewis

(10) Patent No.:    US 12,642,674 B2
(45) Date of Patent:         Jun. 2, 2026

(54) PROSTHETIC COUPLING DEVICE APPARATUS AND METHOD

(71) Applicant: Mark Alan Lewis, Grand Junction, CO (US)

(72) Inventor: Mark Alan Lewis, Grand Junction, CO (US)

(*) Notice: Subject to any disclaimer, the term of this patent is extended or adjusted under 35 U.S.C. 154(b) by 761 days.

(21) Appl. No.: 18/112,022

(22) Filed: Feb. 21, 2023

(65) Prior Publication Data

US 2024/0277492 A1      Aug. 22, 2024

(51) Int. Cl.
   *A61F 2/76*       (2006.01)
   *A61F 2/50*       (2006.01)

(52) U.S. Cl.
   CPC ........ *A61F 2/76* (2013.01); *A61F 2002/5069* (2013.01); *A61F 2002/5072* (2013.01)

(58) Field of Classification Search
   CPC ...... A61F 2002/5067; A61F 2002/5069; A61F 2002/507; A61F 2/585; A61F 2/60; A61F 2/6845; A61F 2/76; A61F 2/7875; A61F 2/7887
   See application file for complete search history.

(56) References Cited

U.S. PATENT DOCUMENTS

| | | | | |
|---|---|---|---|---|
| 3,947,897 A | * | 4/1976 | Owens ..................... | A61F 2/80 623/57 |
| 5,358,524 A | * | 10/1994 | Richelsoph ............... | A61F 2/36 403/46 |
| 2010/0179560 A1 | * | 7/2010 | Chenaux ............... | B25B 23/141 606/104 |

FOREIGN PATENT DOCUMENTS

WO      WO-2021177840 A1 *   9/2021    ............... A61F 2/80

OTHER PUBLICATIONS

Search report (Year: 2024).*

* cited by examiner

*Primary Examiner* — Christie Bahena
(74) *Attorney, Agent, or Firm* — Jeffrey K. Riddle; Riddle IP, PLLC

(57)                ABSTRACT

A prosthetic coupling device includes an internal mount including a proximate shaft portion and a distal mounting portion, a threaded sleeve formed around the distal mounting portion of the internal mount, the threaded sleeve including outer threads, and a rotatable barrel formed around the proximate shaft portion and the distal mounting portion of the internal mount, the rotatable barrel including internal barrel threads that interface with the outer threads of the threaded sleeve. The prosthetic coupling device further includes a detachable coupler formed to fit within the distal mounting portion of the internal mount, the detachable coupler including a coupler detent formed on a radially external surface of the detachable coupler. The prosthetic coupling device further includes a horizontal ball bearing shaft formed through the internal mount, the horizontal ball bearing shaft housing a ball bearing set wherein the ball bearing set interfaces with the coupler detent to lock the detachable coupler to the internal mount when the outer threads of the threaded sleeve are fully seated into the internal barrel threads.

20 Claims, 25 Drawing Sheets

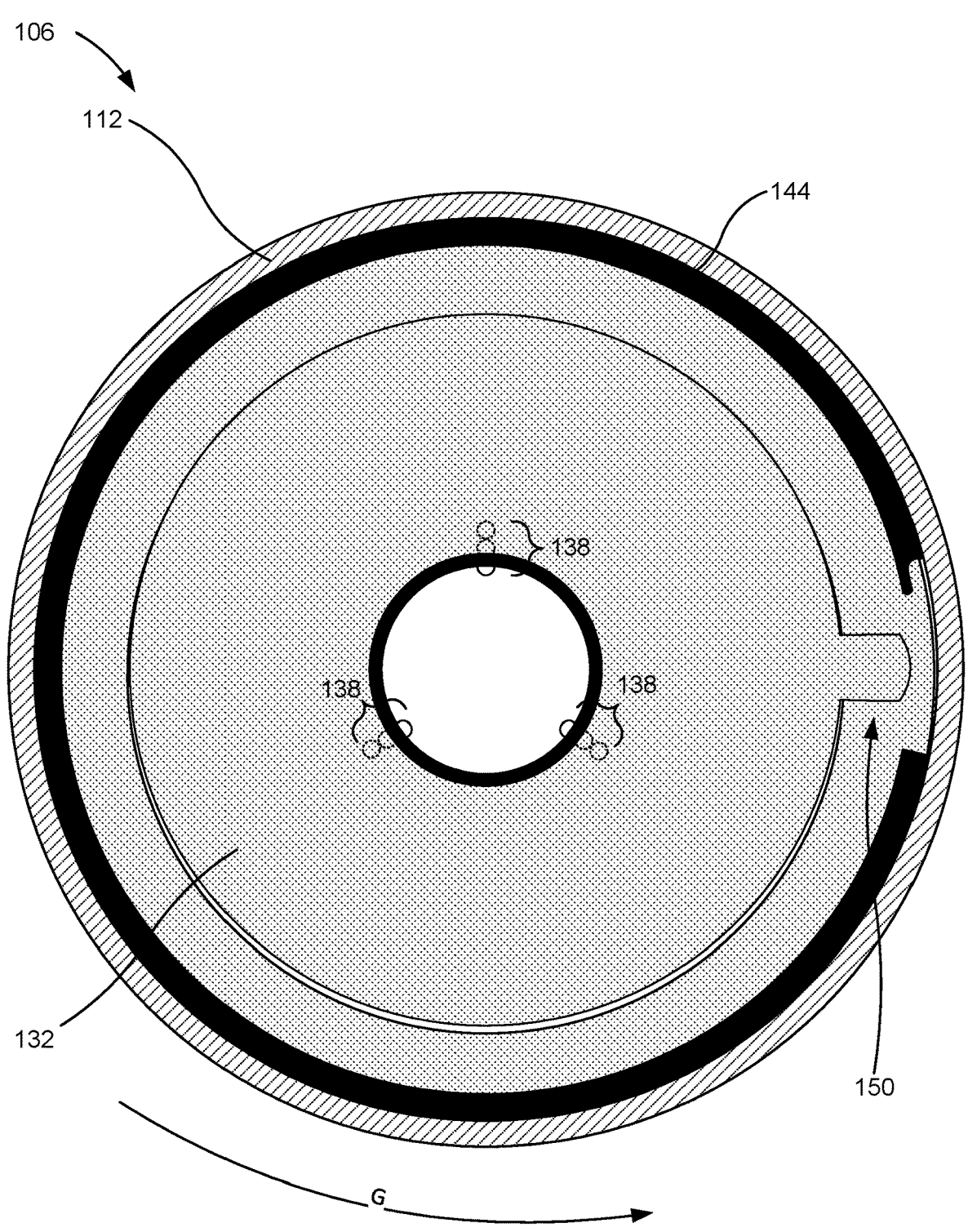
_Fig. 12_

106

166

160

158

160

160

166

166

160

166

106

158      168      160      168      160

166      166

112      116

164

132

144      144

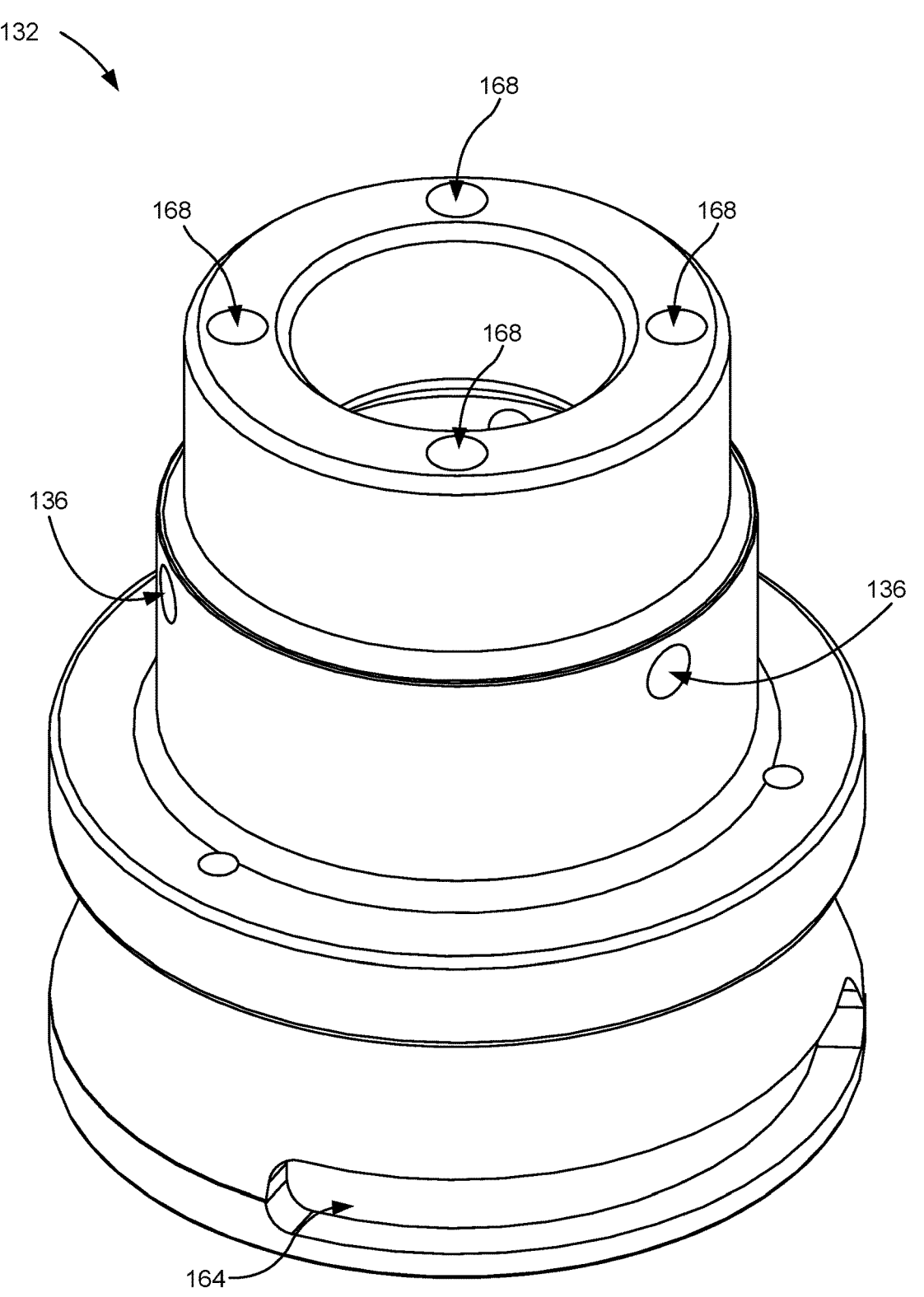
_Fig. 22_

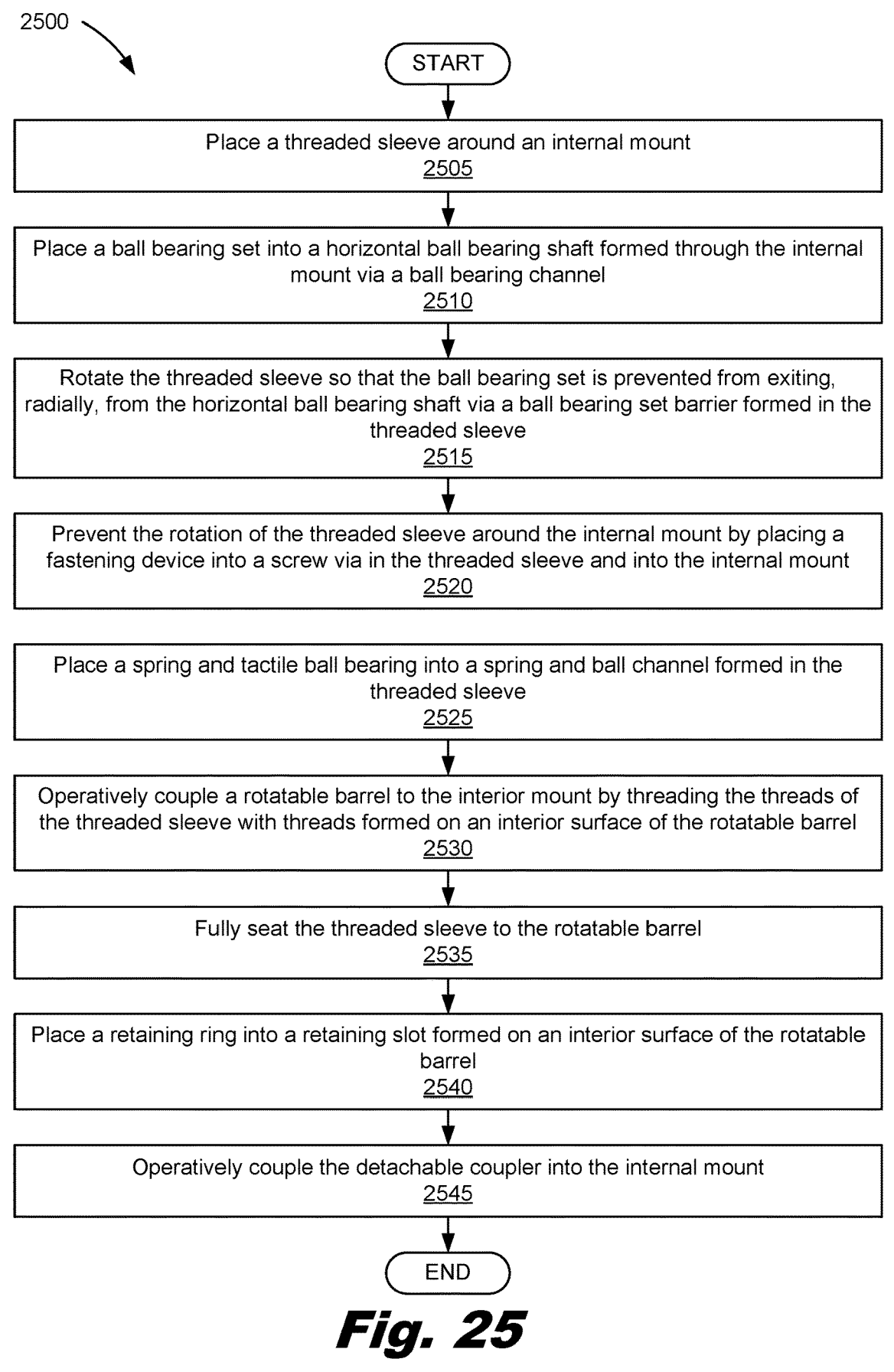

2500

START

Place a threaded sleeve around an internal mount
2505

Place a ball bearing set into a horizontal ball bearing shaft formed through the internal mount via a ball bearing channel
2510

Rotate the threaded sleeve so that the ball bearing set is prevented from exiting, radially, from the horizontal ball bearing shaft via a ball bearing set barrier formed in the threaded sleeve
2515

Prevent the rotation of the threaded sleeve around the internal mount by placing a fastening device into a screw via in the threaded sleeve and into the internal mount
2520

Place a spring and tactile ball bearing into a spring and ball channel formed in the threaded sleeve
2525

Operatively couple a rotatable barrel to the interior mount by threading the threads of the threaded sleeve with threads formed on an interior surface of the rotatable barrel
2530

Fully seat the threaded sleeve to the rotatable barrel
2535

Place a retaining ring into a retaining slot formed on an interior surface of the rotatable barrel
2540

Operatively couple the detachable coupler into the internal mount
2545

END

*Fig. 25*

PROSTHETIC COUPLING DEVICE APPARATUS AND METHOD

FIELD OF THE DISCLOSURE

The present disclosure generally relates to prosthetic devices. The present disclosure more specifically relates to a coupling device to operatively couple parts of a prosthetic device.

BACKGROUND

Proper health care increases the life expectancy of patients. In some cases, patients are born with missing limbs or, due to an accident or a disease, lose a limb. The loss of a limb may require a prosthetic to replace the function of the missing limb so that the patient may realize a better quality of life that without the prosthetic. In the case where the patient has lost a portion of his or her lower extremities such as a lower portion of the patient's leg below the knee or even an upper portion of the leg above the knee, the prosthetic may be used to allow the patient to walk with the use of other mobility aides such as a wheelchair. However, these lower-extremity prosthetic devices must support the weight, be relatively easy to remove, and be comfortable to the patient.

BRIEF DESCRIPTION OF THE DRAWINGS

It will be appreciated that for simplicity and clarity of illustration, elements illustrated in the Figures are not necessarily drawn to scale. For example, the dimensions of some elements may be exaggerated relative to other elements. Embodiments incorporating teachings of the present disclosure are shown and described with respect to the drawings herein, in which:

FIG. 8 is a graphic diagram front view of a rotatable barrel, upper pylon/proximate shaft portion, and a threaded sleeve of the prosthetic coupling device according to another embodiment of the present disclosure;

FIG. 11 is a graphic diagram front view of a rotatable barrel with a retaining ring formed in a retaining ring slot in the rotatable barrel, the upper pylon/proximate shaft portion, and the threaded sleeve of the prosthetic coupling device according to another embodiment of the present disclosure;

FIG. 12 is a graphic diagram bottom view of the rotatable barrel and internal mount of the prosthetic coupling device according to another embodiment of the present disclosure;

FIG. 22 is a side view of an internal mount of a prosthetic coupling device according to another embodiment of the present disclosure;

FIG. 25 is a flow diagram of a method of manufacturing a prosthetic device according to an embodiment of the present disclosure; and The use of the same reference symbols in different drawings may indicate similar or identical items.

DETAILED DESCRIPTION OF THE DRAWINGS

Figure 1:
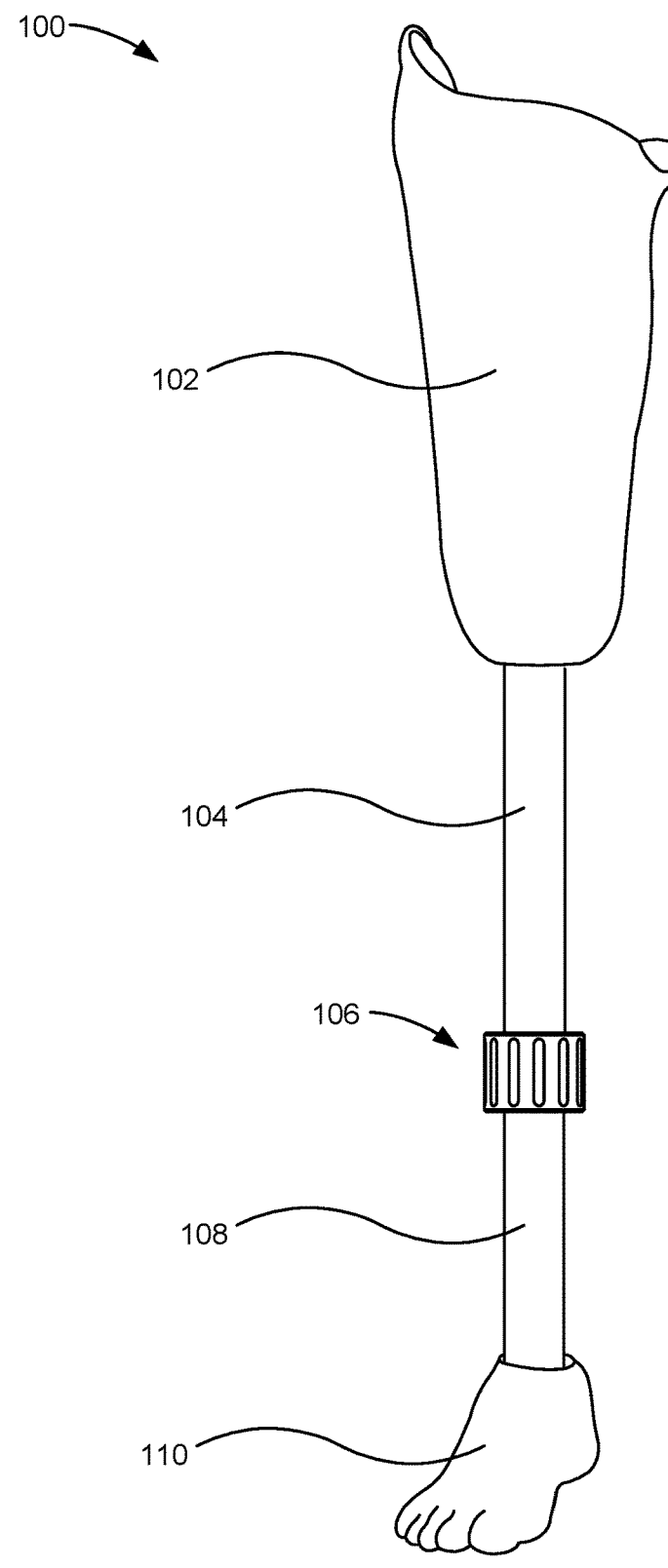
FIG. 1 is a graphic diagram front view of a prosthetic device including a prosthetic coupling device according to an embodiment of the present disclosure.

The following description in combination with the Figures is provided to assist in understanding the teachings disclosed herein. The description is focused on specific implementations and embodiments of the teachings, and is provided to assist in describing the teachings. This focus should not be interpreted as a limitation on the scope or applicability of the teachings.

Prosthetic devices include a variety of artificial devices that replaces a missing body part that was lost due to a disease, condition at birth, or accident. Prosthetic devices restore or provide mobility to those patients that have lost, for example, a limb. Leg prosthetics, for example, allow lower extremity amputee patients to walk instead of using other medical assisting devices such as a wheelchair. Mobility allows such an amputee to live a more self-reliant life that is more fulfilling than without the prosthetic device.

Because prosthetic devices are connected to a patient's body, they may also be removed when not in use. This may require significant manipulation by the patient when putting on and taking off the prosthetic device. Still further, where the prosthetic device is a lower extremity prosthetic device, the patient may put their weight on it requiring that the prosthetic device not only can carry the patient's weight but also include connections that are secured and reliable to the patient. Additionally, the lower extremity prosthetic device may not be formed into a single piece and, instead, may include a plurality of pieces operatively coupled together to form the prosthetic device.

The present specification describes prosthetic coupling device that includes an internal mount including a proximate shaft portion and a distal mounting portion. The prosthetic coupling device also includes a threaded sleeve formed around the distal mounting portion of the internal mount, the threaded sleeve including outer threads. A rotatable barrel is formed around the proximate shaft portion and the distal mounting portion of the internal mount, and the rotatable barrel includes internal barrel threads that interface with the outer threads of the threaded sleeve. The prosthetic coupling device further includes a detachable coupler formed to fit within the distal mounting portion of the internal mount with the detachable coupler including a coupler detent formed on a radially external surface of the detachable coupler. The prosthetic coupling device also includes a horizontal ball bearing shaft formed through the internal mount, the horizontal ball bearing shaft housing a ball bearing set wherein the ball bearing set interfaces with the coupler detent to lock the detachable coupler to the internal mount when the outer threads of the threaded sleeve are fully seated into the internal barrel threads. The prosthetic coupling device described herein allows a patient/user of the prosthetic coupling device (herein referred to as a patient) to remove a lower portion of a prosthetic device by rotating the rotatable barrel. The prosthetic coupling device may be used to easily remove the lower portion of the prosthetic device and, in some example embodiments, replace the lower portion with another lower portion. For example, the detachable coupler and a lower pylon and prosthetic foot coupled to the detachable coupler may be replaced with another detachable coupler and lower pylon assembly that includes a specific type of footwear coupled to the lower pylon. This allows a patient to swap out lower assemblies of the prosthetic device by operation of the prosthetic coupling device described herein. Additionally, the operation of the prosthetic coupling device is relatively quick and prevents any accidental release of the detachable coupler from the internal mount while also bearing the weight of the patient.

In an embodiment, a spring and ball channel is formed vertically into a top surface of the threaded sleeve to house a spring and tactile ball bearing. In an embodiment, a plurality of interior barrel detents are also formed on an interior surface of the rotatable barrel to engage with the tactile ball bearing to provide tactile rotational feedback to the patient when the rotatable barrel is rotated by the patient. This allows a patient to feel the actuation of the rotation of the rotatable barrel so that the patient can feel the coupling of the internal mount to the detachable coupler.

In an embodiment, the prosthetic coupling device further includes a retaining ring slot formed in an interior surface of the rotatable barrel and a retaining ring formed into the retaining ring slot to prevent the rotatable barrel from being fully unscrewed from the internal mount and threaded sleeve. This retaining ring prevents the disassembly of the rotatable barrel from the internal mount by the patient during use of the prosthetic coupling device. In an embodiment, the placement of the retaining ring, the placement of the retaining ring slot, and a thickness of the retaining ring sets the rotational distance of the rotatable barrel.

During operation of the prosthetic coupling device the patient may rotate the rotatable barrel to disengage the internal mount from the detachable coupler. In an embodiment, the ball bearing set disengages with the coupler detent formed in the detachable coupler to unlock the detachable coupler from the internal mount when the outer threads of the threaded sleeve are not fully seated relative to the rotatable barrel and into the internal barrel threads due to the patient rotating the rotatable barrel in a rotational direction.

In an embodiment, the prosthetic coupling device includes a registering slot to receive a registration pin formed on the detachable coupler to align the detachable coupler radially relative to the internal mount. This prevents the patient from coupling the distal portion of the prosthetic coupling device at an incorrect radial angle relative to the proximal portion of the prosthetic coupling device.

In an embodiment, the threaded sleeve comprising a ball bearing channel to, during assembly of the prosthetic coupling device, conduct the ball bearing set into the horizontal ball bearing shaft. The threaded sleeve also includes a ball bearing set barrier to, when the threaded sleeve is rotated around the proximate shaft portion of the internal mount, prevent the ball bearing set from exiting, radially, from the horizontal ball bearing shaft. An internal end of the horizontal ball bearing shaft, in an embodiment, has an internal diameter smaller than a diameter of the ball bearing set to prevent the ball bearing set from exiting the ball bearing shaft at the internal end.

FIG. 1 is a graphic diagram front view of a prosthetic device 100 including a prosthetic coupling device 106 according to an embodiment of the present disclosure. FIG. 1 shows the prosthetic device 100 as a lower extremity prosthetic device that serves as a right leg or leg portion used by a patient to walk with and put the patient's weight on. It is appreciated, however, that in other embodiments, the prosthetic coupling device 106 described herein may be used to operatively couple any portion of any other type of prosthetic device. Additionally, the coupling device may be used to couple any pylon or two objects together and the present specification contemplates the use of the prosthetic coupling device 106 described herein for these other purposes. For ease of description and understanding, the prosthetic coupling device 106 is described herein as a lower extremity or leg prosthetic device. With reference to FIG. 1 and other figures in the present application, a distal end of the prosthetic device 100 is the end of the prosthetic device 100 furthest from the patient and includes the foot 110. Similarly, the use of the term "distal" when describing other devices of the prosthetic device 100 including the prosthetic coupling device is meant to be understood as a location on these devices that are furthest from the patient when the patient is wearing the prosthetic device 100. Similarly, the use of the term "proximate" when describing other devices of the prosthetic device 100 including the prosthetic coupling device is meant to be understood as a location on these devices that are closest to the patient when the patient is wearing the prosthetic device 100.

As shown in FIG. 1, the prosthetic device 100 includes a socket 102 portion. The socket 102 serves as an interface between the residual limb of the patient and the prosthetic device 100. In the example embodiment shown in FIG. 1, the socket 102 allows a patient to place his or her residual portion of a limb into the socket 102 which may be adjusted for fit and comfort for the patient/amputee. The socket 102 may include other securing devices such as straps to operatively couple the socket 102 to the patient's residual limb.

The socket 102, in an embodiment, may be operatively coupled to an upper pylon/proximate shaft portion 104 of the prosthetic device 100. In an embodiment, the upper pylon/proximate shaft portion 104 may be made of a durable material such as metal that can bear the weight of the patient. Such materials may include titanium, aluminum, copper, steel, magnesium, alloys of these metals, along with other metals. In an embodiment, the upper pylon/proximate shaft portion 104 may be made of carbon-fiber weave or carbon-fiber-reinforced polymer. The present specification further contemplates that wall thicknesses of the lower pylon 108, the upper pylon 104, the internal mount described herein (e.g., FIG. 2, 132 for example), and the detachable coupler (e.g., FIG. 2, 140 for example) may be selected to provide a sufficient structural integrity to withstand the weight from the patient and the structural strains placed on the prosthetic device 100 and the prosthetic coupling device 106.

In an embodiment, the length of the upper pylon/proximate shaft portion 104 of the prosthetic device 100 may be selected based on the patient's ability to access the prosthetic coupling device 106 shown in FIG. 1. In an embodiment, the length of the upper pylon/proximate shaft portion 104 combined with the length of a lower pylon 108 and a height of the prosthetic foot 110 may also be selected based on the length of the patient's other length so that the total length of the prosthetic device 100 may match the length of the patient's other leg. It is appreciated that, where the patient is a double amputee in their lower extremities, the length of the prosthetic device 100 described herein may match the length of the other prosthetic device 100. In an embodiment, the length of the upper pylon/proximate shaft portion 104 as well as the length of the lower pylon 108 and height of the prosthetic foot 110 may be determined and selected by a doctor or other prosthetic building professional.

As described herein, the prosthetic device 100 includes the prosthetic coupling device 106 described herein. The prosthetic coupling device 106 couples a first portion of the prosthetic device 100 to a second portion of the prosthetic device 100. In the example embodiment, shown in FIG. 1, the prosthetic coupling device 106 operatively couples the upper pylon/proximate shaft portion 104 to the lower pylon 108 with its prosthetic foot 110. It is appreciated, as well, that the prosthetic coupling device 106 does not need to be operatively coupled to an upper pylon 104 and a lower pylon 108 and can, instead be coupled directly to a proximate or distal end of a prosthetic limb. In an example embodiment, various attachment scenarios allow for the prosthetic coupling device 100 to be directly coupled to the socket 102 or the foot 110.

As described herein, the prosthetic coupling device 106 is configured to secure the upper pylon/proximate shaft portion 104 to the lower pylon 108 via a rotation of a rotatable barrel of the prosthetic coupling device 106. This relatively quick action of rotating the rotatable barrel allows a patient to quickly uncouple and couple the lower pylon 108 to the upper pylon/proximate shaft portion 104. In an embodiment, multiple lower pylon 108 and prosthetic foot 110 combinations may be owned by the patient. In an example embodiment, the patient may own a first lower pylon 108 and prosthetic foot 110 that has a first type of shoe on the prosthetic foot 110 such as a tennis shoe or sneaker. In this example embodiment, the patient may also own a second lower pylon 108 and prosthetic foot 110 combination that includes a dress shoe on the prosthetic foot 110. With the prosthetic coupling device 106, the patient may easily switch from the first lower pylon 108 and prosthetic foot 110/shoe combination with the second lower pylon 108 and prosthetic foot 110/shoe by rotating the rotatable barrel of the prosthetic coupling device 106 in a first direction, removing the first lower pylon 108 and prosthetic foot 110/shoe combination from the prosthetic coupling device 106, inserting the second lower pylon 108 and prosthetic foot 110/shoe combination into the prosthetic coupling device 106, and turning the rotatable barrel in a second direction to lock the second lower pylon 108 and prosthetic foot 110/shoe combination to the prosthetic coupling device 106 and the upper portions of the prosthetic device 100. It is also clear that other, differently fitted, lower pylon 108 and prosthetic foot 110 combinations may be owned by the patient to quickly switch out different footwear when needed. Additionally, the prosthetic coupling device 106 allows the patient to know when the lower pylon 108/prosthetic foot 110 and securely locked to the prosthetic coupling device 106 when a maximum rotation (e.g., a quarter turn rotation) of the rotatable barrel is completed. Additionally, the rotation of the rotatable barrel of the prosthetic coupling device 106 includes tactile feedback so that the patient may feel that the rotatable barrel is rotating.

The lower pylon 108 is used to operatively couple the prosthetic foot 110 to the prosthetic coupling device 106 and the upper pylon/proximate shaft portion 104 and socket 102. In an embodiment, the lower pylon 108 may be made of a durable material such as metal that can bear the weight of the patient. Such materials may include titanium, aluminum, copper, steel, magnesium, alloys of these metals, along with other metals. In an embodiment, the upper pylon/proximate shaft portion 104 may be made of carbon-fiber weave or carbon-fiber-reinforced polymer. The lower pylon 108 may be operatively coupled to a prosthetic foot 110 or other distal part of the prosthetic device 100 such as a running blade using other types of mechanical coupling devices.

Figure 2:
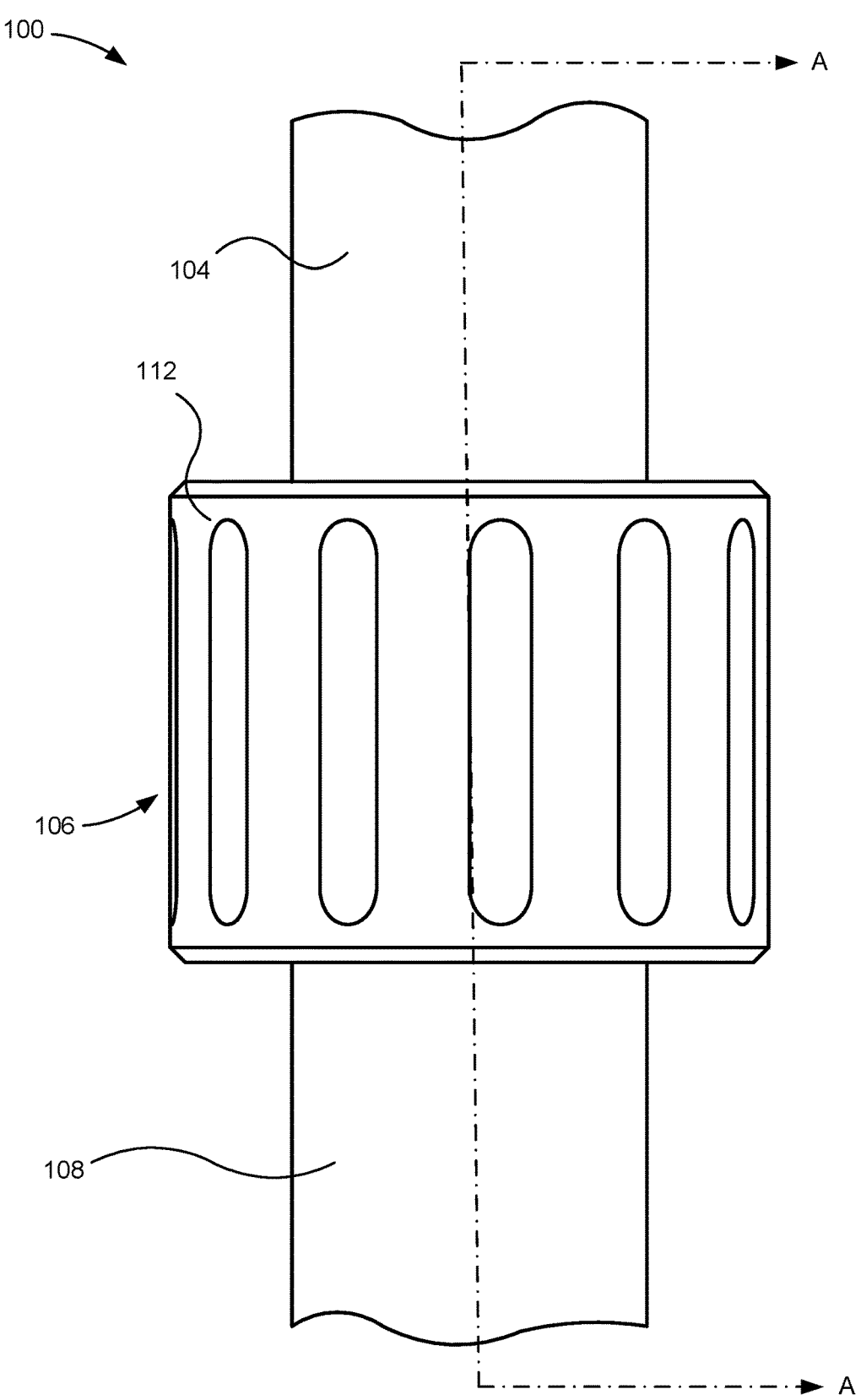
FIG. 2 is a graphic diagram front view of a prosthetic coupling device according to an embodiment of the present disclosure.

FIG. 2 is a graphic diagram front view of a prosthetic coupling device 106 according to an embodiment of the present disclosure. FIG. 2 shows that the upper pylon/proximate shaft portion 104 is operatively coupled to an internal mount (not shown) of the prosthetic coupling device 106. The upper pylon/proximate shaft portion 104 may, in an embodiment, for a monolithic part with the internal mount described herein. FIG. also shows that a lower pylon 108 is operatively coupled to a detachable coupler (not shown) of the prosthetic coupling device 106. In an embodiment, the lower pylon 108 forms a monolithic part with detachable coupler as described herein.

During operation, the patient may couple the lower pylon 108 and the detachable coupler (not shown) to the remaining portions of the prosthetic coupling device 106 including the upper pylon/proximate shaft portion 104 by inserting the detachable coupler into the bottom side of the prosthetic coupling device 106. The patient may then rotate the rotatable barrel 112 in a first direction (e.g., clockwise from the perspective of the patient above the rotatable barrel 112 in an embodiment) to lock the detachable coupler to the internal mount within the prosthetic coupling device 106. To remove the lower pylon 108 and the detachable coupler from the internal mount, the patient may rotate the rotatable barrel 112 in a second direction (e.g., counterclockwise from the perspective of the patient above the rotatable barrel 112). As described herein, this easy connection of the lower pylon 108 to and decoupling of the lower pylon 108 from the prosthetic coupling device 106 allows the patient to easily remove this portion of the prosthetic device 100 and, in an embodiment, replace it with a different lower portion of the prosthetic device 100 as described herein. It is appreciated, however, that this prosthetic device 100 may be used for different prosthetic devices and the present specification contemplates the use of these other uses of the prosthetic coupling device 106 described herein.

Figure 3:
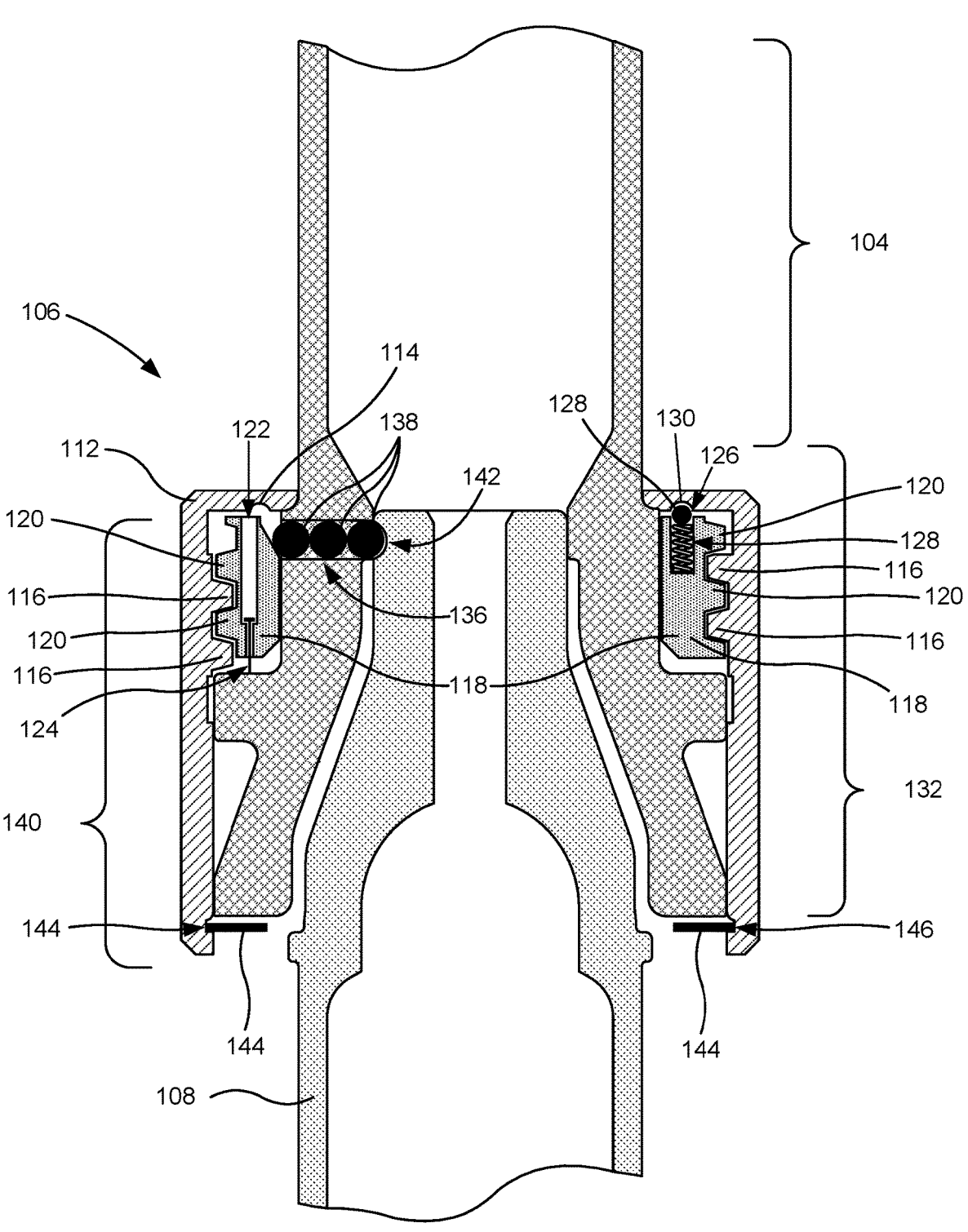
FIG. 3 is a graphic diagram, side, cross-section view of the prosthetic coupling device according to an embodiment of the present disclosure.

FIG. 2 also includes a section line "A" indicating a cross-sectional plane of the prosthetic coupling device 106 shown in FIG. 3. FIG. 3 is, therefore, a graphic diagram, side, cross-section view of the prosthetic coupling device along the section plane as indicated by section line "A" in FIG. 2 according to an embodiment of the present disclosure. Again, FIG. 3 shows the upper pylon 104 forming a monolithic piece with the internal mount 132 and the lower pylon 108 forming a monolithic piece with the detachable coupler 140. In an embodiment, the lower pylon 108 may be coupled to the detachable coupler 140 via a welding process. In an embodiment, the upper pylon 104 may be coupled to the internal mount 132 via a welding process. It is appreciated, however, that the lower pylon may be coupled to the detachable coupler 140 and the upper pylon 104 may be coupled to the internal mount 132 via other mechanical coupling devices that can provide an operative connection that can withstand the weight of the patient as the patient, in this embodiment, walks with the prosthetic coupling device 106. These other coupling methods include, but are not limited to, clamps, glues, bonding agents, etc. In an embodiment, the upper pylon 104 may be friction welded to the internal mount 132 and the lower pylon 108 may be friction welded to the to the detachable coupler 140. It is appreciated that components of the prosthetic coupling device 106 described herein may also be fastened together using an industrial glue and the present specification contemplates the use of these types of glues. An example of an industrial glue that can be used to couple one or more components of the prosthetic coupling device 106 together may include 3M® Scotch-Weld® epoxy adhesive DP420 or DP 420NS or similar types of glues, epoxy, or chemical adhesives. Scotch-Weld® is a registered trademark of the 3M corporation of Maplewood, Minnesota.

The internal mount 132 includes a threaded sleeve 118 formed around a portion of the internal mount 132. The threaded sleeve 118 is formed into a ring around the internal mount 132. The internal mount 132 may include a shelf that prevents the threaded sleeve 118 from moving a distance along the outer surface of the internal mount 132. This shelf may also be a location where the threaded sleeve 118 is operatively coupled to the internal mount 132 via, for example, a screw 124. In an embodiment, the screw 124 may be passed through a screw via 122 and screwed into an upper surface of the shelf formed around the internal mount 132. In an embodiment, the screw 124 may be partially screwed into the shelf such that the threaded sleeve 118 may move, vertically, a specific distance along the outer surface of the internal mount 132. A height of the screw head of the screw 124 may be set such that a maximum vertical distance that the threaded sleeve 118 is allowed to move is set. It is appreciated that the screw 124 may be any type of screw that does or does not include a head including a set screw. Further, it is appreciated that the length and diameter (e.g., either major diameter or minor diameter) of the screw 124 may vary depending on the physical dimensions of the threaded sleeve 118 as well as other components of the prosthetic coupling device 106. Further, it is appreciated that the length and diameter (e.g., either major diameter or minor diameter) of the screw 124 may vary depending on the ability of the screw 124 to couple the threaded sleeve 118 to the internal mount 132 as described herein.

The threaded sleeve 118 further includes outer threads 120 that interface with a set of internal barrel threads 116 of the rotatable barrel 112. The helical slop and lead of the internal barrel threads 116 and the outer threads 120 may vary and may be set such that a minimum rotational distance of the rotatable barrel 112 by the patient in order to lock and unlock the detachable coupler 140 to the internal mount 132 of the prosthetic coupling device 106. In an embodiment, the outer threads 120 of the threaded sleeve 118 and the internal barrel threads 116 of the rotatable barrel 112 may be right-handed threads that follows the right-hand grip rule. However, it is appreciated that in other embodiments, the direction of the outer threads 120 and internal barrel threads 116 may have an opposite threaded direction known as the left-handed thread direction. The right-handedness of the outer threads 120 and internal barrel threads 116 allows for, in the embodiment shown in FIG. 3, the rotation of the rotatable barrel 112 clockwise (e.g., as viewed from above by the patient) to lock the detachable coupler 140 into the internal mount 132 and the rotation of the rotatable barrel 112 counterclockwise (e.g., as viewed from above by the patient) to unlock the detachable coupler 140 from the internal mount 132.

In an embodiment, as the outer threads 120 of the threaded sleeve 118 engage and are threaded through the internal barrel threads 116 of the rotatable barrel 112 in a clockwise manner, a top surface of the threaded sleeve 118 is allowed to move closer to an interior surface of a top portion of the rotatable barrel 112. The full rotation of the rotatable barrel 112, therefore, causes the rotatable barrel 112 to be fully seated with the threaded sleeve 118 when the rotatable barrel 112 is rotated in a counterclockwise direction. The full seating of the threaded sleeve 118 relative to the rotatable barrel 112 causes the threaded sleeve 118 to be lifted away from the shelf of the internal mount 132 a distance allowed by the length of the screw 124 as described in an embodiment herein. The embodiment shown in FIG. 3, the prosthetic coupling device 106 is in a locked orientation with the threaded sleeve 118 fully seated against the internal top surface of the rotatable barrel 112. It is appreciated, however, that the movement of the threaded sleeve 118 (e.g., fully seated with the rotatable barrel 112 or not) may not limit the rotation of the rotatable barrel 112 and other components of the prosthetic coupling device 106 may provide a maximum or minimum rotation of the rotatable barrel 112. These other components may include, in an example embodiment, the retaining ring 144, the internal mount 132, and the rotatable barrel 112 as well as the interaction between these components as well. As described herein in FIGS. 16 and 22-24, for example, other components (e.g., rotational set screw 162 and set screw channel 164) may be used to prevent over rotation of the rotatable barrel 112 and thereby creating over torquing of the rotatable barrel 112 against the internal mount 132 and other components of the prosthetic coupling device 106 in an embodiment.

During operation, as the threaded sleeve 118 is seated fully against the interior top surface of the rotatable barrel 112 as shown in FIG. 3, a sloped face formed on the interior surface of the threaded sleeve 118 forces individual ball bearings of a ball bearing set 138 towards the detachable coupler 140. This locks the detachable coupler 140 to the internal mount 132 as the ball bearing set 138 engages the coupler detent 142 with the rotatable barrel 112 moved towards the threaded sleeve 118. The ball bearing set 138, in the embodiment shown in FIG. 3, includes three ball bearings that are allowed to pass along a horizontal ball bearing shaft 136 formed through the internal mount 132. Although FIG. 3 shows that the ball bearing set 138 includes three ball bearings, the present specification contemplates the use of any number of ball bearings having any radius to form the ball bearing set 138 with varying diameters of the horizontal ball bearing shaft 136 to accommodate those numbers of ball bearings with a specific radius as well as the thickness of the walls of the internal mount 132. It is further appreciated that locking mechanisms may be placed within the horizontal ball bearing shaft 136 such as a locking pin and the present specification contemplates that these other mechanical devices, moved by the sloped surface of the threaded sleeve pushes these types of mechanical devices to interface with the coupler detent 142 as described herein.

The ball bearing set 138 is prevented from fully exiting the horizontal ball bearing shaft 136 by a necked portion of the horizontal ball bearing shaft 136 formed closest to an interior surface of the detachable coupler 140. This necked portion of the horizontal ball bearing shaft 136 allows a portion of one of the ball bearings of the ball bearing set 138 to stick out and pass into a coupler detent 142 formed into an outer surface of the detachable coupler 140. In an embodiment, three sets of ball bearing sets 138 formed in three horizontal ball bearing shafts 136 may be used to press the ball bearings of the ball bearing sets 138 into their respective coupler detents 142 formed in the outer surface of the detachable coupler 140. However, the present specification contemplates that more or less ball bearing sets 138 may be used to couple the detachable coupler 140 to the internal mount 132 of the prosthetic coupling device 106 according to the principles described herein.

During operation, as the threaded sleeve 118 is seated fully against the interior top surface of the rotatable barrel 112 as shown in FIG. 3, a tactile ball bearing 130 engages with a plurality of interior barrel detents 114 formed on an interior surface of a top end of the rotatable barrel 112. The tactile ball bearing 130 is pressed against the interior surface of the rotatable barrel 112 by a spring 128. The tactile ball bearing 130 and the spring 128 may be placed within a spring and ball channel 126. The spring and ball channel 126 is formed in a vertical direction so that a distal end of the spring 128 may press against an interior lower wall of the spring and ball channel 126 in order to also press the tactile ball bearing 130 against the interior barrel detents 114 of the rotatable barrel 112 as described herein. In an embodiment, therefore, the spring 128 is biased to force the tactile ball bearing 130 against the interior surface of the rotatable barrel 112 and into the plurality of interior barrel detents 114. The plurality of interior barrel detents 114 may be formed along the interior surface of the rotatable barrel 112 such that as the patient rotates the rotatable barrel 112, the tactile ball bearing 130 is forced out of a first interior barrel detent 114, rolled toward a second interior barrel detent 114 and is pressed into the second interior barrel detent 114 providing tactile feedback to the patient. This process continues as the tactile ball bearing 130 passes along the individual interior barrel detents 114 providing tactile feedback to the patient. Additionally, the force imparted onto the tactile ball bearing 130 and into the interior barrel detents 114 by the spring 128 may provide additional resistive force that prevents unintended or unwanted rotation of the rotatable barrel 112 unless the patient is rotating the rotatable barrel 112. The rotative force the patient imparts on the rotatable barrel 112 overcomes this resistive force imparted by the spring 128 against the tactile ball bearing 130 and interior barrel detents 114. Although FIG. 3 shows a single spring and ball channel 126 with a spring 128 and tactile ball bearing 130, the present specification contemplates that multiple spring and ball channels 126 may be formed into the threaded sleeve 118.

The prosthetic coupling device 106 further includes a retaining ring 144 placed within a retaining ring slot 146 formed on a lower interior surface of the rotatable barrel 112. The placement of the retaining ring 144 may be based on the length of the internal mount 132 such that the retaining ring slot 146 is formed below the lowest end of the internal mount 132. The retaining ring 144, in an embodiment, prevents the rotatable barrel 112 from being removable by the patient during operation. In the example embodiment shown in FIG. 3, the counterclockwise rotation of the rotatable barrel 112 (e.g., when the patient is unlocking the detachable coupler 140 from the internal mount 132) causes the rotatable barrel 112 to move upwards. This movement of the rotatable barrel 112 upwards causes the lowest portion of the internal mount 132 to abut or be adjacent to the retaining ring 144 preventing the complete removal of the rotatable barrel 112 from the prosthetic coupling device 106. Additionally, by preventing the removal of the rotatable barrel 112 from the internal mount 132 and threaded sleeve 118 by the retaining ring 144, the spring 128 and tactile ball bearing 130 are kept in place.

Figure 4:
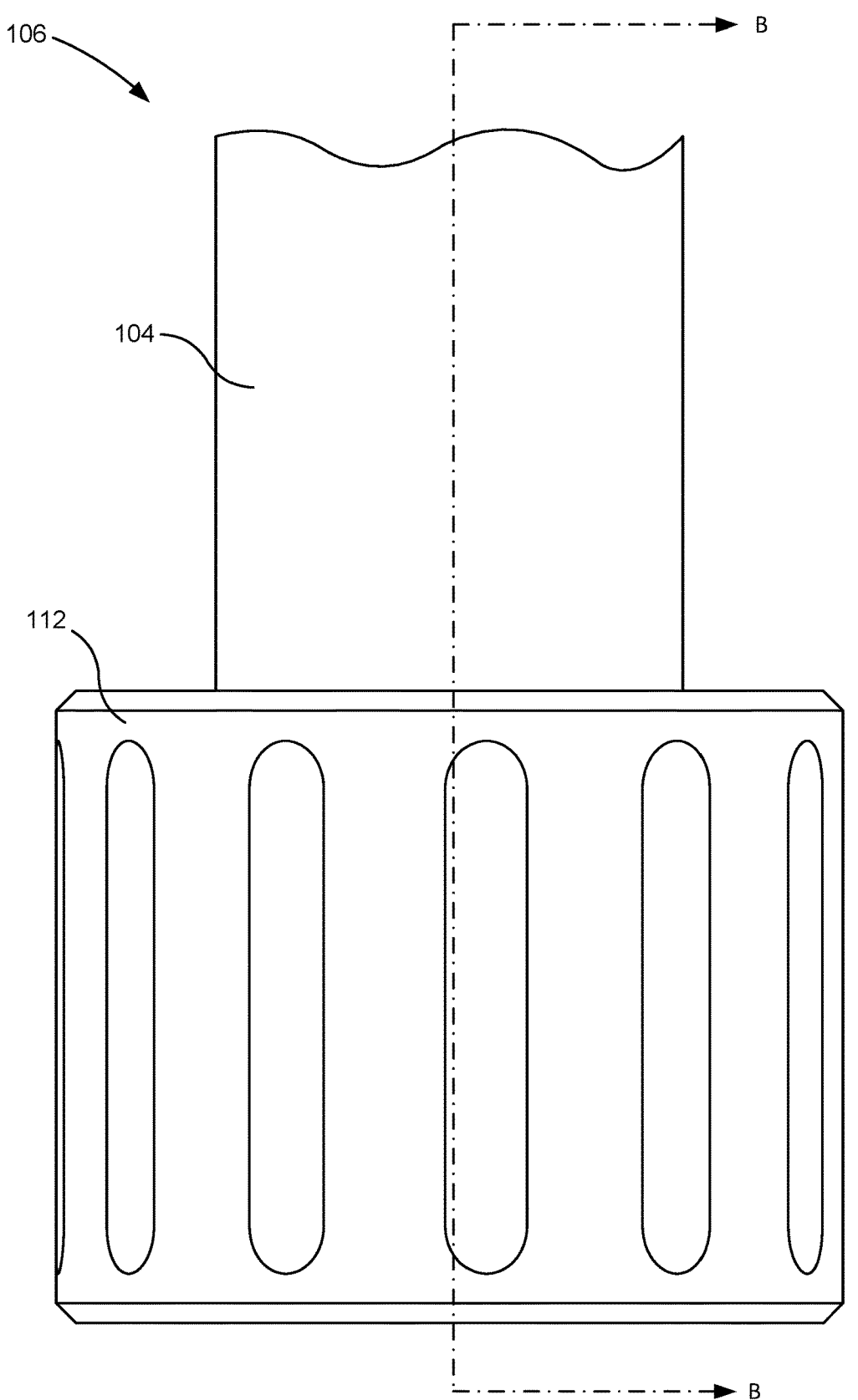
FIG. 4 is a graphic diagram side view of a rotatable barrel, upper pylon/proximate shaft portion, and an internal mount of the prosthetic coupling device according to an embodiment of the present disclosure.

FIG. 4 is a graphic diagram side view of a rotatable barrel 112, upper pylon 104 and/or proximate shaft portion, and an internal mount (not shown) of the prosthetic coupling device 106 according to an embodiment of the present disclosure. FIG. 4 shows the rotatable barrel 112 rotated in a counterclockwise direction that causes the detachable coupler (not shown) to be removed from the prosthetic coupling device 106. Additionally, as described herein, the internal mount abuts the retaining ring (not shown) as a result of the internal barrel threads (not shown) of the rotatable barrel (not shown) and the outer threads (not shown) of the threaded sleeve (not shown) being unthreaded as described in connection with FIG. 3.

Figure 5:
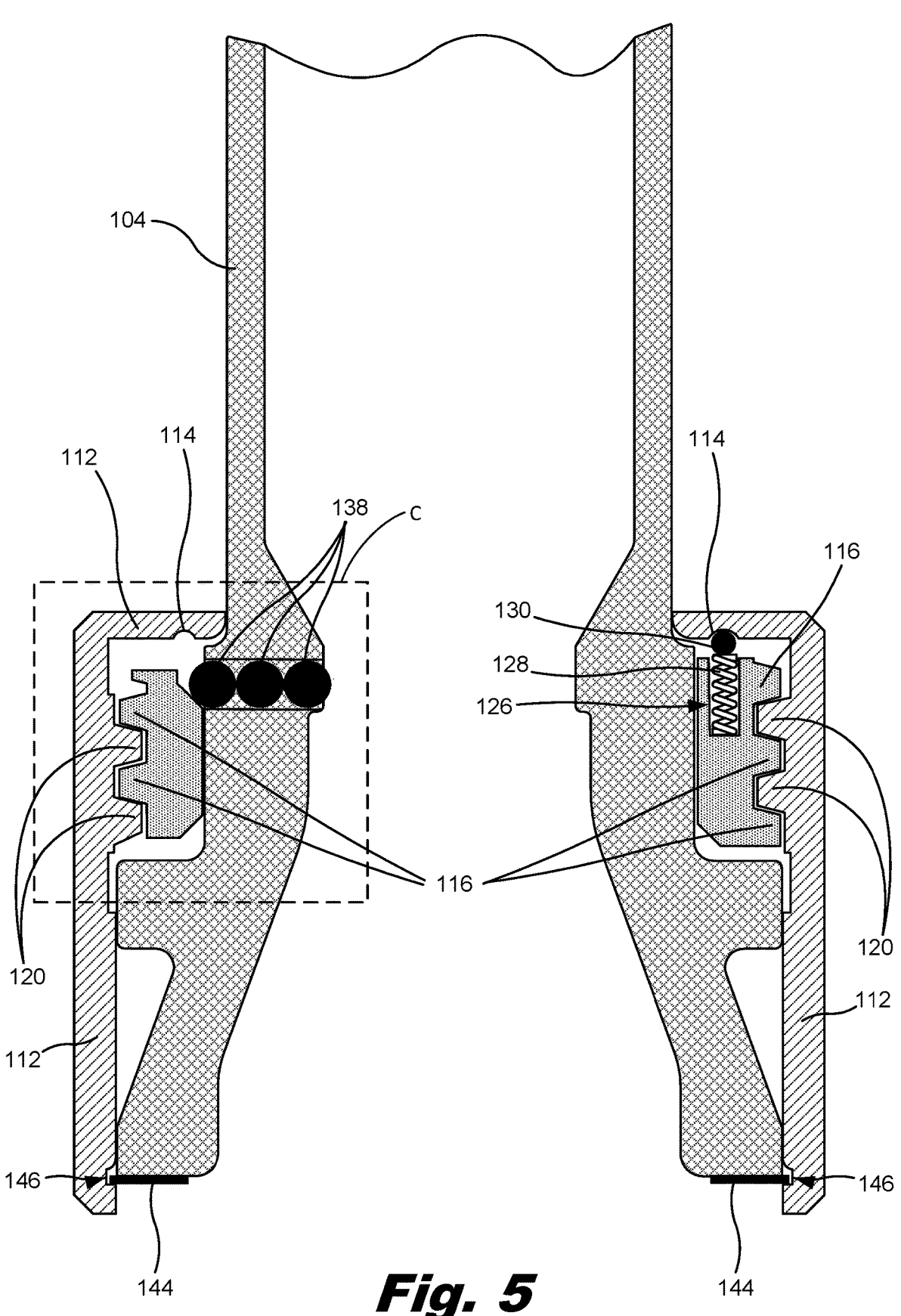
FIG. 5 is a graphic diagram, side, cross-section view of a rotatable barrel, upper pylon/proximate shaft portion, and an internal mount of the prosthetic coupling device according to another embodiment of the present disclosure.

FIG. 4 also includes a section line "B" indicating a cross-sectional plane of the prosthetic coupling device 106 shown in FIG. 5. FIG. 5 is a graphic diagram, side, cross-section view of a rotatable barrel, upper pylon/proximate shaft portion, and an internal mount of the prosthetic coupling device according to another embodiment of the present disclosure. As described herein, the rotatable barrel 112 has been rotated in a counterclockwise direction (e.g., as viewed from the top of the prosthetic coupling device 106 by the patient) such that the lowest portion of the internal mount 132 has abutted the retaining ring 144. As described herein, the retaining ring 144 being placed in the retaining ring slot 146 is used to prevent the complete decoupling of the rotatable barrel 112 from the internal mount 132 and threaded sleeve 118.

Figure 6:
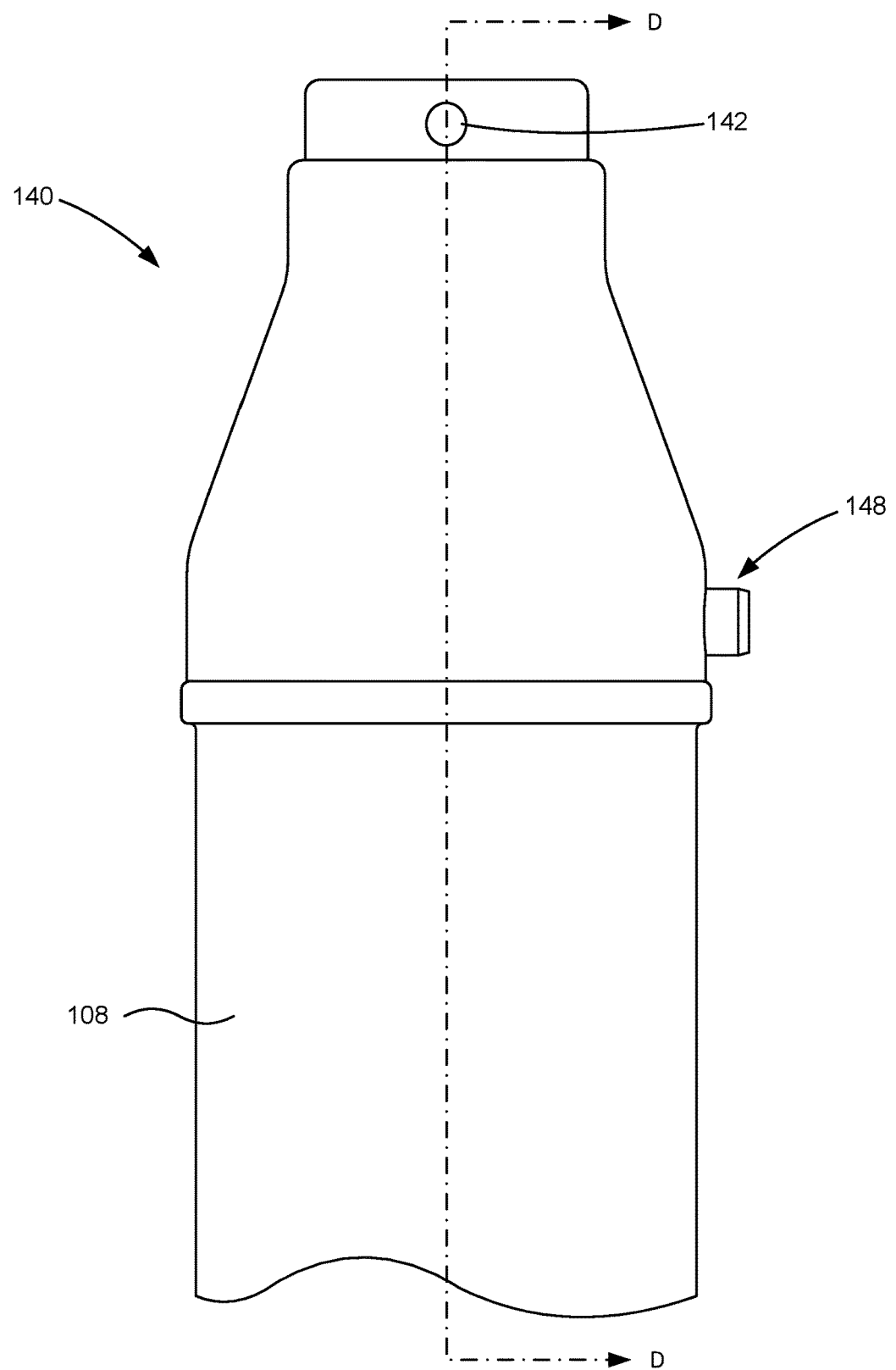
FIG. 6 is a graphic diagram side view of a detachable coupler of the prosthetic coupling device according to an embodiment of the present disclosure.

As the rotatable barrel 112 is rotated in a counterclockwise direction as described, the threaded sleeve 118 also drops lower within the prosthetic coupling device 106. This lowering of the threaded sleeve 118 allows the ball bearing set 138 to pass through the horizontal ball bearing shaft 136 and towards the threaded sleeve 118. In the example embodiment shown in FIG. 5, a sloped face of the threaded sleeve 118 that once pushed the ball bearing set 138 into the horizontal ball bearing shaft 136 and into the coupler detents (e.g., FIG. 3, 142) is now lowered allowing more space for the ball bearing set 138 to move outward and away from the detachable coupler (not shown). Because the ball bearing set 138 locked the detachable coupler into the prosthetic coupling device 106 as seen in FIG. 3, the removal of the ball bearing set 138 from the coupler detents of the detachable coupler allows the detachable coupler to be removed as shown in FIG. 5. In an embodiment, the rotational distance that the patient rotates the rotatable barrel 112 in order for the rotatable barrel 112 to travel the distance to abut against the retaining ring 144 is a quarter turn. In this embodiment, the patient may turn or rotate the rotatable barrel 112 a quarter turn counterclockwise to unlock the detachable coupler 140 from the internal mount 132 and a quarter turn clockwise to lock the detachable coupler 140 into the internal mount 132. It is appreciated that the distance the that internal mount 132 is from the retaining ring 144 placed into the retaining ring slot 146 on the rotatable barrel 112 may determine the rotational distance necessary for the patient to unlock and lock the detachable coupler 140 from and to the internal mount 132. The greater the distance that the bottom surface of the internal mount 132 is from the retaining ring 144, the more rotational distance is necessary for the patient to unlock and lock the detachable coupler 140 from and to the internal mount 132. The opposite is also true such that the shorter the distance that the bottom surface of the internal mount 132 is from the retaining ring 144, the less rotational distance is necessary for the patient to unlock and lock the detachable coupler 140 from and to the internal mount 132. In an embodiment, the distance that the internal mount 132 is from the retaining ring 144 determines the maximum rotational distance of the rotatable barrel 122 but when the detachable coupler 140 (FIG. 3) is placed within the internal mount 132, the maximum rotational distance is set by the distance the ball bearing set 138 moves into the coupler detents (e.g., 142. FIG. 6) when attaching the detachable coupler 140 to the internal mount 132.

However, as described herein, the complete removal of the rotatable barrel 112 from the threaded sleeve 118 is prevented by the incorporation of the retaining ring 144 into the retaining ring slot 146. A complete counterclockwise rotation of the rotatable barrel 112 causes the lowest portion of the internal mount 132 to abut the retaining ring 144 preventing further rotation of the rotatable barrel 112. Additionally, by preventing the decoupling of the rotatable barrel 112 from the threaded sleeve 118 and internal mount 132, the spring 128 and tactile ball bearing 130 placed into the spring and ball channel 126 may be maintained in place. This further allows the haptic feedback to be felt by the patient when rotating the rotatable barrel 112 (e.g., as the tactile ball bearing 130 passes from one interior barrel detent 114 to another) as well as provide resistance to the rotation of the rotatable barrel 112 unless and until the user applies the sufficient rotation force to rotate the rotatable barrel 112.

FIG. 5 also does not show the screw via and screw used to secure the threaded sleeve 118 to the internal mount 132. In the embodiment shown in FIG. 5, the cross-section view is taken along a plane where the spring and ball channel 126, the spring 128, and tactile ball bearing 130 (e.g., one of many in an embodiment) by the screw via and screw (e.g., one of many formed into the threaded sleeve 118 and internal mount 132). It is appreciated that the location, orientation, and number of sets of screw vias and screws as well as the location, orientation, and number of sets of spring and ball channels 126, springs 128, and tactile ball bearings 130 may vary and the present specification contemplates these various locations, orientations, and numbers of these devices formed into the threaded sleeve 118 and the prosthetic coupling device 106.

Still further, although FIG. 5 shows a single horizontal ball bearing shaft 136 with a single ball bearing set 138, the present specification contemplates that the internal mount 132 may include a plurality of horizontal ball bearing shafts 136, each with a ball bearing set 138 formed therein. In an embodiment, the number of horizontal ball bearing shafts 136 formed into the internal mount 132 and the number of ball bearing sets 138 placed therein may match a number of coupler detents (not shown) formed into the detachable coupler 140. In an embodiment, the placement of the horizontal ball bearing shafts 136 and ball bearing sets 138 may match, radially, the location of the coupler detents formed in the detachable coupler (not shown).

Figure 10:
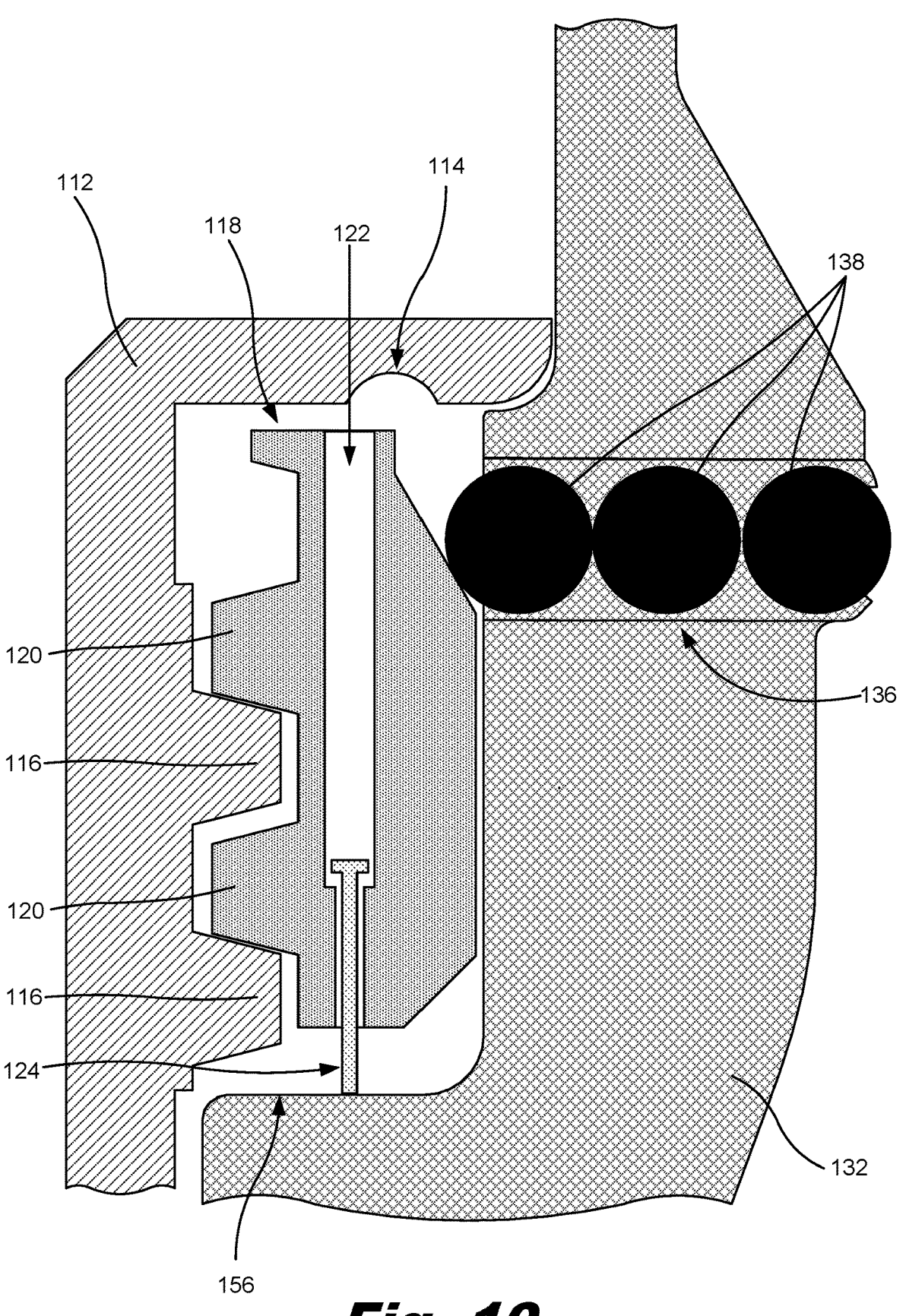
FIG. 10 is a graphic diagram cross-section of the rotatable barrel, internal mount with a ball bearing set in a horizontal ball bearing shaft, and threaded sleeve with a screw via according to an embodiment of the present disclosure.

FIG. 5 also shows a window "C" drawn around a portion of the rotatable barrel 112, a portion of the threaded sleeve 118, and a portion of the internal mount 132 where the horizontal ball bearing shaft 136 is formed and the ball bearing set 138 is placed. Window "C" is represented in FIG. 10 and will be described in more detail herein.

FIG. 6 is a graphic diagram side view of a detachable coupler 140 of the prosthetic coupling device 106 according to an embodiment of the present disclosure. In an embodiment, the detachable coupler 140 is operatively coupled to a lower pylon 108 via, for example, a welding process among other coupling processes described herein. As described herein, the lower pylon 108 may then be coupled to a distal portion of the prosthetic device such as a foot or a blade among other prosthetic devices.

The detachable coupler 140 shown in FIG. 6 includes one or more coupler detents 142. As described herein, the number and radial position of each of the coupler detents 142 formed into the detachable coupler 140 may match the number and radial position of the horizontal ball bearing shaft (not shown) and ball bearing sets (not shown) that are formed into the internal mount of the prosthetic coupling device described herein. As described herein, the coupler detents 142 may be a detent that forms a location where a terminal ball bearing of the ball bearing set may be seated. In an embodiment, the terminal ball bearing of the ball bearing set 138 is seated into the coupler detent 142 as the detachable coupler 140 is seated into the internal mount of the prosthetic coupling device 106 and the patient has rotated the rotatable barrel (not shown) as described herein (e.g., described in connection with FIG. 3).

The detachable coupler 140 further includes, in an embodiment, a registering post 148 formed on an outside surface of the detachable coupler 140. The registering post 148 is used by the patient to properly align the detachable coupler 140 relative to the internal mount (not shown) of the prosthetic coupling device 106. In an embodiment, the registering post 148 interfaces with a registering slot (not shown) formed into a bottom edge of the internal mount of the prosthetic coupling device 106. This alignment of the detachable coupler 140 relative to the internal mount prevents the patient from misaligning the lower pylon 108 and foot (or another prosthetic terminal device) relative to the upper pylon described in FIG. 1. Once aligned, the patient may lock the detachable coupler to the internal mount of the prosthetic coupling device as described herein (e.g., rotating the rotatable barrel 112) in order to be able place weight on the prosthetic coupling device 106/prosthetic device and walk properly using the prosthetic device.

In an embodiment, the outer surface of the detachable coupler 140 may be formed to fit within the internal mount of the prosthetic coupling device 106. In an embodiment, the outer surface of the detachable coupler 140 may form an engineering fit with the interior surface of the internal mount of the prosthetic coupling device. This engineering fit may have a predefined tolerance that considers the strains that may be presented to the internal mount, the detachable coupler 140, the ball bearing set, and other surfaces and devices within the prosthetic coupling device. In an example embodiment, the outer surface of the detachable coupler forms a clearance fit with the interior surface of the internal mount. In an example embodiment, the outer surface of the detachable coupler forms a loose running, a free running, a close running, a sliding, or a location clearance fit with the interior surface of the internal mount. The engineering fit may be set such that the outer surface of the detachable coupler 140 and the inner surface of the internal mount may touch so that weight of the patient may be distributed across more surface area within the prosthetic coupling device. It is appreciated that other types of engineering fits may be used, and the present specification contemplates the use of these different engineering fits.

Figure 7:
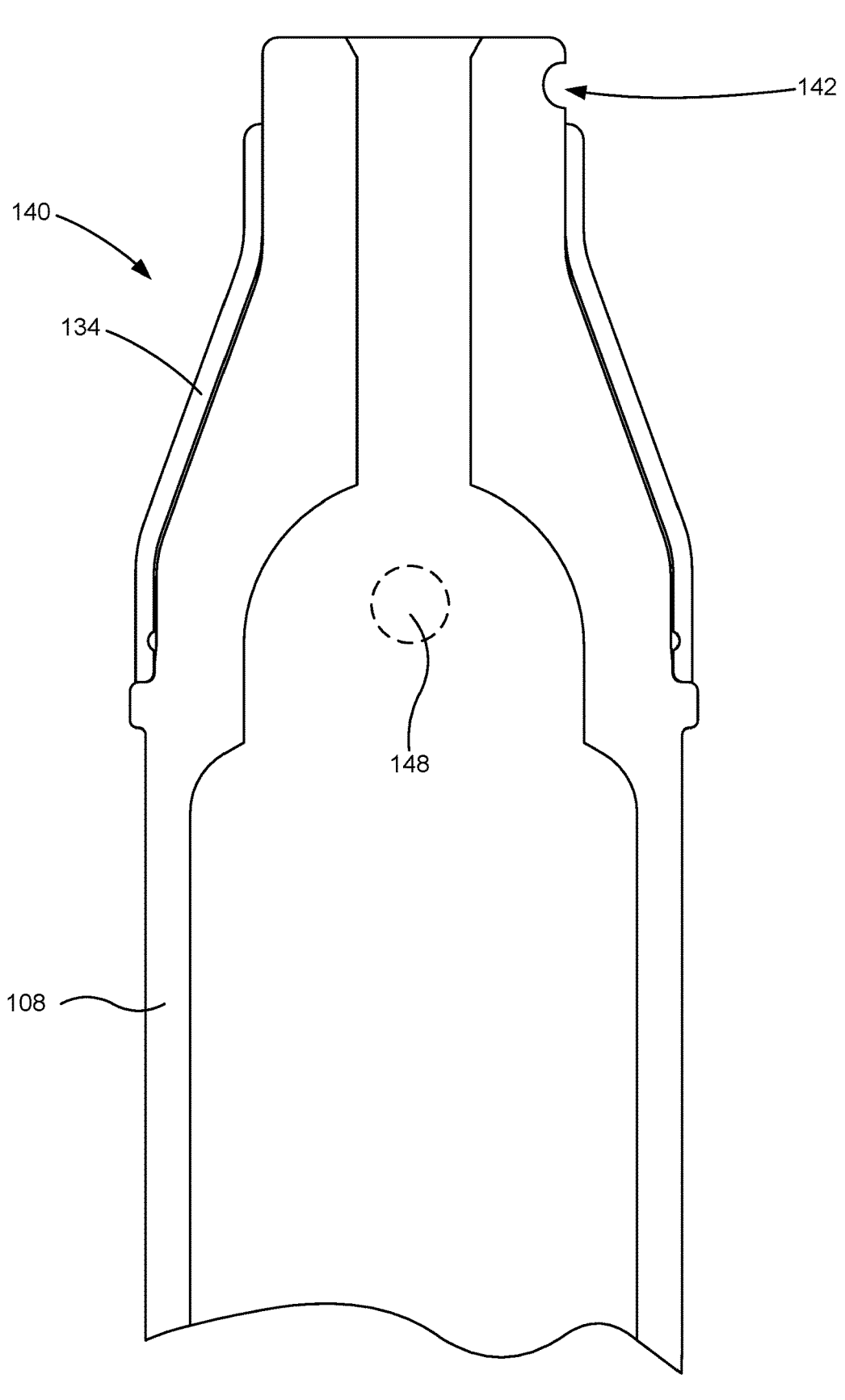
FIG. 7 is a graphic diagram front, cross-section view of a detachable couple of the prosthetic coupling device according to another embodiment of the present disclosure.

FIG. 6 also includes a section line "D" indicating a cross-sectional plane of the detachable coupler 140 shown in FIG. 7. FIG. 7 is a graphic diagram front view of detachable coupler 140 of the prosthetic coupling device 106 according to another embodiment of the present disclosure. FIG. 7 shows that the coupler detent 142 is formed into an upper portion of the detachable coupler 140. The coupler detent 142, as described herein, is formed to fit a portion of a leading ball bearing of the ball bearing set. In an example embodiment, the necked portion of the horizontal ball bearing shaft described in connection with FIG. 3 may allow less than half of the leading ball bearing of the ball bearing set to extend out of the horizontal ball bearing shaft 136. This amount of leading ball bearing of the ball bearing set may be pressed into the coupler detent 142 when the patient has locked the detachable coupler 140 into the internal mount as described herein. In an embodiment, the leading ball bearing of the ball bearing set may form an engineering fit with the coupler detent 142. This engineering fit between this leading ball bearing and the internal surfaces of the coupler detent 142 may be a loose running, a free running, a close running, a sliding, or a location clearance fit such the detachable coupler 140 is not removeable from the internal mount when the patient has locked the detachable coupler 140 into the internal mount. It is appreciated that the single coupler detent 142 shown in FIG. 7 may not be the only coupler detent 142 formed on the detachable coupler 140 in an embodiment. In an embodiment, the detachable coupler 140 may include three coupler detents 142 that each interface with a ball bearing set as described herein.

The detachable coupler 140 further includes a registering post 148 formed on an outside surface of the internal mount 132. In the embodiment shown in FIG. 7, the registering post 148 is welded to the outer surface of the detachable coupler 140. It is appreciated that in other embodiments the post 148 is operatively coupled to the outer surface of the detachable coupler 140 via any means including press fitting, for example. Again, the registering post 148 is used by the patient to properly align the detachable coupler 140 relative to the internal mount (not shown) of the prosthetic coupling device. In an embodiment, the registering post 148 interfaces with a registering slot (not shown) formed into a bottom edge of the internal mount of the prosthetic coupling device 106. This alignment of the detachable coupler 140 relative to the internal mount prevents the patient from misaligning the lower pylon 108 and foot (or another prosthetic terminal device) relative to the upper pylon described in FIG. 1. Once aligned, the patient may lock the detachable coupler to the internal mount of the prosthetic coupling device as described herein (e.g., rotating the rotatable barrel) in order to be able place weight on the prosthetic coupling device/prosthetic device and walk properly using the prosthetic device.

The detachable coupler 140 further includes an outer plastic sleeve 134 formed on an outer surface of the detachable coupler 140. This outer plastic sleeve 134 may be milled to fit around the outer surface of the detachable coupler 140. In an embodiment, the outer plastic sleeve 134 may be injection molded onto the detachable coupler 140. In an embodiment, the outer plastic sleeve 134 may be made of Acetal or other similar material that has a low surface energy that has a relatively high wear resistance and high strength. The low surface energy of the outer plastic sleeve 134 allows the detachable coupler to be easily slid into and out of the internal mount 132 of the prosthetic coupling device 106 during operation by a user. The high strength and wear resistance allows for the multiple coupling and uncoupling of the detachable coupler 140 from the internal mount 132 of the prosthetic coupling device 106 with reduced amounts of wear and tear between the detachable coupler 140 and the internal mount 132. In an embodiment, the outer plastic sleeve 134 may be coupled to the outer surface of the detachable coupler 140 via a glue or other adhesive. In an embodiment, the glue or adhesive may include RelTek® Bondit® B-4682TH or other similar adhesives that adhere the outer plastic sleeve 134 to the metal (e.g. aluminum such as 2024-T351 aluminum and similar alloys) of the detachable coupler 140. The inclusion of the outer plastic sleeve 134 acts as a lubricant, facilitating easy separation of detachable coupler 140 from the internal mount 132 of the prosthetic coupling device 106 for easier use by the user. Additionally, it is appreciated that other types of plastics or materials different from the acetal plastic of the outer plastic sleeve 134 and the present specification contemplates the use of these other plastics. In an embodiment, for example, a brass sleeve 134 could also provide similar advantages as the acetal plastic of the outer plastic sleeve 134.

Figure 8:
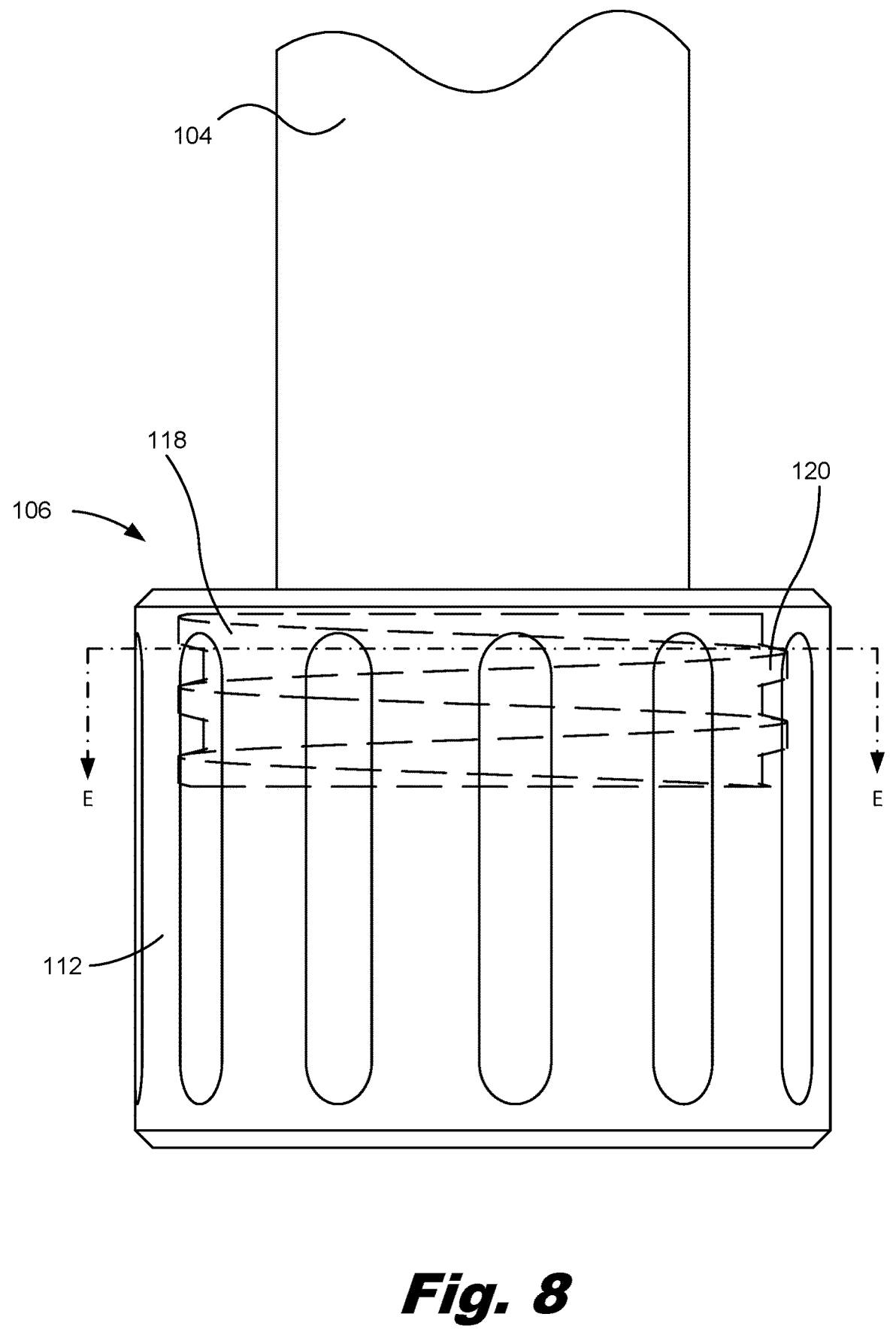

FIG. 8 is a graphic diagram front view of a rotatable barrel 112, upper pylon/proximate shaft portion 104, and a threaded sleeve 118 of the prosthetic coupling device according to another embodiment of the present disclosure. FIG. 8 shows the threaded sleeve 118 in dashed lines to show the relative position of the threaded sleeve 118 within the rotatable barrel 112.

As described herein, the outer threads 120 of the threaded sleeve 118 (and the internal barrel threads of the rotatable barrel as described herein) may be right-handed threads that follows the right-hand grip rule. However, it is appreciated that in other embodiments, the direction of the outer threads 120 (and internal barrel threads) may have an opposite threaded direction known as the left-handed thread direction. The right-handedness of the outer threads 120 shown in FIG. 8 allows for the rotation of the rotatable barrel 112 clockwise (e.g., as viewed from above by the patient) to lock the detachable coupler (not shown) into the internal mount (not shown) and the rotation of the rotatable barrel 112 counterclockwise (e.g., as viewed from above by the patient) to unlock the detachable coupler from the internal mount.

Figure 9:
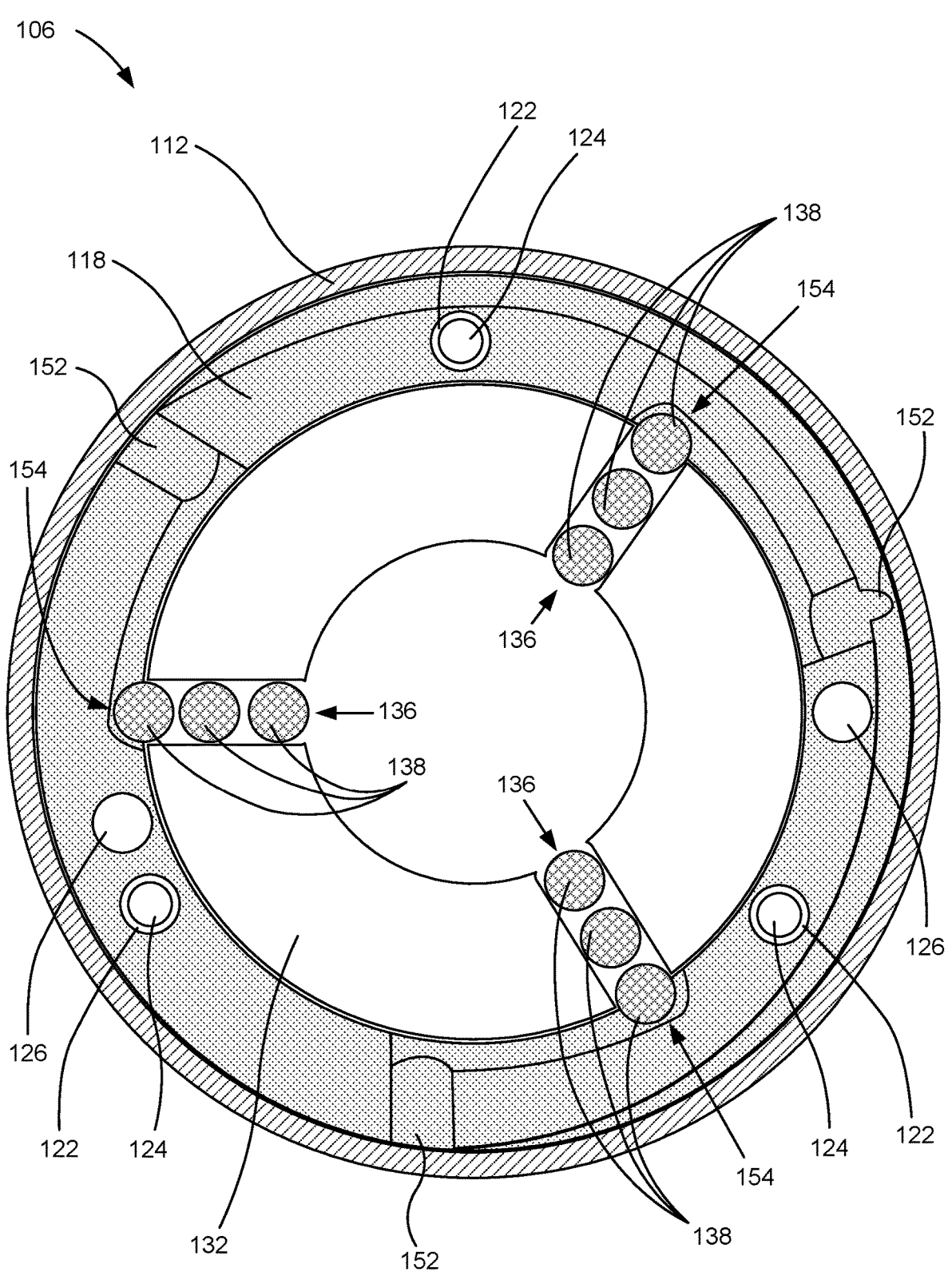
FIG. 9 is a graphic diagram, top, cross-section view of the rotatable barrel, upper pylon/proximate shaft portion, threaded sleeve, and an internal mount of the prosthetic coupling device according to another embodiment of the present disclosure.

FIG. 8 also includes a section line "E" indicating a cross-sectional plane of the rotatable barrel 112 and threaded sleeve 118 shown in FIG. 9. FIG. 9 is a graphic diagram, bottom, cross-section view of the rotatable barrel 112, threaded sleeve 118, and an internal mount 132 of the prosthetic coupling device 106 according to another embodiment of the present disclosure. FIG. 9 shows the arrangement of the ball bearing sets 138 with the horizontal ball bearing shafts 136 as well as a ball bearing channel 152 formed in the threaded sleeve 118.

As described herein, a screw 124 may be passed through a screw via 122 formed into the threaded sleeve 118 and screwed into an upper surface of the shelf formed around the internal mount 132. In an embodiment, the screw 124 may be partially screwed into the shelf such that the threaded sleeve 118 may move, vertically (or in the perspective of FIG. 9, in and out of the page), a specific distance along the outer surface of the internal mount 132. A height of a screw head of the screw 124 may be set such that a maximum vertical distance that the threaded sleeve 118 is allowed to move is set. In some embodiments, a headless screw may be used as the screw 124. FIG. 9 shows that the threaded sleeve 118 may be secure to the shelf of the internal mount 132 using three screws 124. However, the present specification contemplates that the number of screws 124 used to secure the threaded sleeve 118 to the shelf of the internal mount 132 may be less than or more than three.

As described herein, the threaded sleeve 118 may include one or more spring and ball channels 126 that each include a spring 128 and tactile ball bearing 130 as described herein. The spring and ball channels 126 are formed in a vertical direction so that a distal end of each of the springs may press against an interior lower wall of their respective spring and ball channels 126 in order to also impart a force against the tactile ball bearing. This, in turn, presses the tactile ball bearing against the interior barrel detents (not shown) of the rotatable barrel 112 as described herein. In an embodiment, therefore, the springs are each biased to force the tactile ball bearings against the interior surface of the rotatable barrel 112 and into the plurality of interior barrel detents 114. The plurality of interior barrel detents 114 may be formed along the interior surface of the rotatable barrel 112 such that as the patient rotates the rotatable barrel 112, the tactile ball bearings are forced out from one interior barrel detent 114, rolled toward another interior barrel detent 114, and is pressed into the other interior barrel detent 114 providing tactile feedback to the patient. This process continues as each of the tactile ball bearings passes along the individual interior barrel detents 114 providing tactile feedback to the patient. Additionally, the force imparted onto the tactile ball bearings and into the interior barrel detents 114 by the springs provide additional resistive force that prevents unintended or unwanted rotation of the rotatable barrel 112 unless the patient is rotating the rotatable barrel 112. The rotative force the patient imparts on the rotatable barrel 112 overcomes this resistive force imparted by the springs against the tactile ball bearings and interior barrel detents 114. Although FIG. 9 shows three spring and ball channels 126 that each are equipped with a spring and tactile ball bearing, the present specification contemplates that multiple spring and ball channels 126 may be formed into the threaded sleeve 118.

As described herein, the internal mount 132 includes one or more horizontal ball bearing shafts 136 that each include a ball bearing set 138. The ball bearing sets 138 may each include a leading ball bearing closest to a terminal end of the horizontal ball bearing shafts 136 closest to a center point of the internal mount 132. Because the terminal end of the horizontal ball bearing shafts 136 have a necked portion, the leading ball bearing of the ball bearing set 138 is allowed to extend out of the horizontal ball bearing shaft 136 but not entirely out of the horizontal ball bearing shaft 136. Because this necked portion of the horizontal ball bearing shaft 136 allows a portion of the leading ball bearing of the ball bearing set 138 to stick out of the horizontal ball bearing shaft 136 a distance, the leading ball bearing may pass into a coupler detent (not shown) formed into an outer surface of the detachable coupler (not shown) as described herein. In the embodiment shown in FIG. 9, three sets of ball bearing sets 138 are formed in three horizontal ball bearing shafts 136 and are used to press the leading ball bearings of the ball bearing sets 138 to extend into their respective coupler detents formed in the outer surface of the detachable coupler. However, the present specification contemplates that more or less ball bearing sets 138 may be used to couple the detachable coupler to the internal mount 132 of the prosthetic coupling device according to the principles described herein.

The threaded sleeve 118 further includes features used to assemble the internal mount 132 and threaded sleeve 118 with the ball bearing sets 138. Among these features are a ball bearing channel 152. The ball bearing channel 152 may be used to guide each of the ball bearings into their respective horizontal ball bearing shafts 136 during assembly. During the assembly process, in an example embodiment, the ball bearing channels 152 may be aligned with their respective horizontal ball bearing shafts 136 prior to the screws 124 being inserted into their screw vias 122 to secure the threaded sleeve 118 to the shelf of the internal mount 132. When the ball bearing channels 152 are aligned with their respective horizontal ball bearing shafts 136, a manufacturer may direct the ball bearing sets 138 to be inserted into their respective horizontal ball bearing shafts 136. Once the ball bearing sets 138 have been inserted into their respective horizontal ball bearing shafts 136, the threaded sleeve 118 may be rotated such that a ball bearing set barrier 154 formed into the threaded sleeve 118 prevents the ball bearings of the ball bearing sets 138 from exiting the horizontal ball bearing shaft 136 at a terminal end closest to the rotatable barrel 112. In FIG. 9, the threaded sleeve 118 is rotated clockwise in order to place the ball bearing set barrier 154 behind the ball bearing sets 138. At this point, the screws 124 may be inserted into their respective screw vias 122 to secure the threaded sleeve 118 to the internal mount 132 at the orientation shown in FIG. 9.

FIG. 10 is a graphic diagram cross-section of the rotatable barrel 112, internal mount 132 with a ball bearing set 138 in a horizontal ball bearing shaft 136, and threaded sleeve 118 with a screw via 122 and screw 124 according to an embodiment of the present disclosure. As described herein, FIG. 10 is a reproduction of window "C" shown in FIG. 5.

As described herein, the internal mount 132 of the prosthetic coupling device 106 includes a threaded sleeve 118 formed around a portion of the internal mount 132. The threaded sleeve 118 is formed into a ring around the internal mount 132. The internal mount 132 may include a shelf 156 that prevents the threaded sleeve 118 from moving a distance, downward, along the outer surface of the internal mount 132. This shelf 156 may also be a location where the threaded sleeve 118 is operatively coupled to the internal mount 132 via, for example, a screw 124. In an embodiment, the screw 124 may be passed through a screw via 122 and screwed into an upper surface of the shelf 156 formed around the internal mount 132. In an embodiment, the screw 124 may be partially screwed into the shelf 156 such that the threaded sleeve 118 may move, vertically, a specific distance along the outer surface of the internal mount 132. A height of the screw head of the screw 124 may be set such that a maximum vertical distance that the threaded sleeve 118 is allowed to move is set. FIG. 10 shows that the maximum vertical distance of the threaded sleeve 118 has not been reached because the threaded sleeve 118 has not been fully seated against an interior surface of the rotatable barrel 112. Additionally, a space is present between the head of the screw 124 and a bottom surface of the screw via 122.

During operation, as the threaded sleeve 118 interacts with the internal barrel threads 116 of the rotatable barrel 112 as shown in FIG. 3, for example, a sloped face formed on the interior surface of the threaded sleeve 118 forces individual ball bearings of a ball bearing set 138 towards a terminal end of the horizontal ball bearing shaft 136 closest to the detachable coupler (not shown). This locks the detachable coupler to the internal mount 132 as the ball bearing set 138 engages the coupler detent (not shown) with the rotatable barrel 112 fully seated to the threaded sleeve 118. The ball bearing set 138, in the embodiment shown in FIG. 10, includes three ball bearings that are allowed to pass along a horizontal ball bearing shaft 136 formed through the internal mount 132. Although FIG. 10 shows that the ball bearing set 138 includes three ball bearings, the present specification contemplates the use of any number of ball bearings having any radius to form the ball bearing set 138 with varying diameters of the horizontal ball bearing shaft 136 to accommodate those numbers of ball bearings with a specific radius as well as the thickness of the walls of the internal mount 132.

FIG. 10 further shows an interior barrel detent 114. As described herein, the spring and ball channel (not shown) is formed in a vertical direction through the threaded sleeve 118 so that a distal end of the spring (not shown) may press against an interior lower wall of the spring and ball channel in order to also press the tactile ball bearing (not shown) against the interior barrel detents 114 of the rotatable barrel 112 as described herein. In an embodiment, therefore, the spring is biased to force the tactile ball bearing against the interior surface of the rotatable barrel 112 and into the plurality of interior barrel detents 114. The plurality of interior barrel detents 114 may be formed along the interior surface of the rotatable barrel 112 such that as the patient rotates the rotatable barrel 112, the tactile ball bearing is forced out of a first interior barrel detent 114, rolled toward a second interior barrel detent 114 and is pressed into the second interior barrel detent 114 providing tactile feedback to the patient. This process continues as the tactile ball bearing passes along the individual interior barrel detents 114 providing tactile feedback to the patient. Additionally, the force imparted onto the tactile ball bearing and into the interior barrel detents 114 by the spring may provide additional resistive force that prevents unintended or unwanted rotation of the rotatable barrel 112 unless the patient is rotating the rotatable barrel 112. The rotative force the patient imparts on the rotatable barrel 112 overcomes this resistive force imparted by the spring against the tactile ball bearing and interior barrel detents 114. Although FIG. 10 shows a single spring and ball channel with a spring and tactile ball bearing, the present specification contemplates that multiple spring and ball channels may be formed into the threaded sleeve 118.

Figure 11:
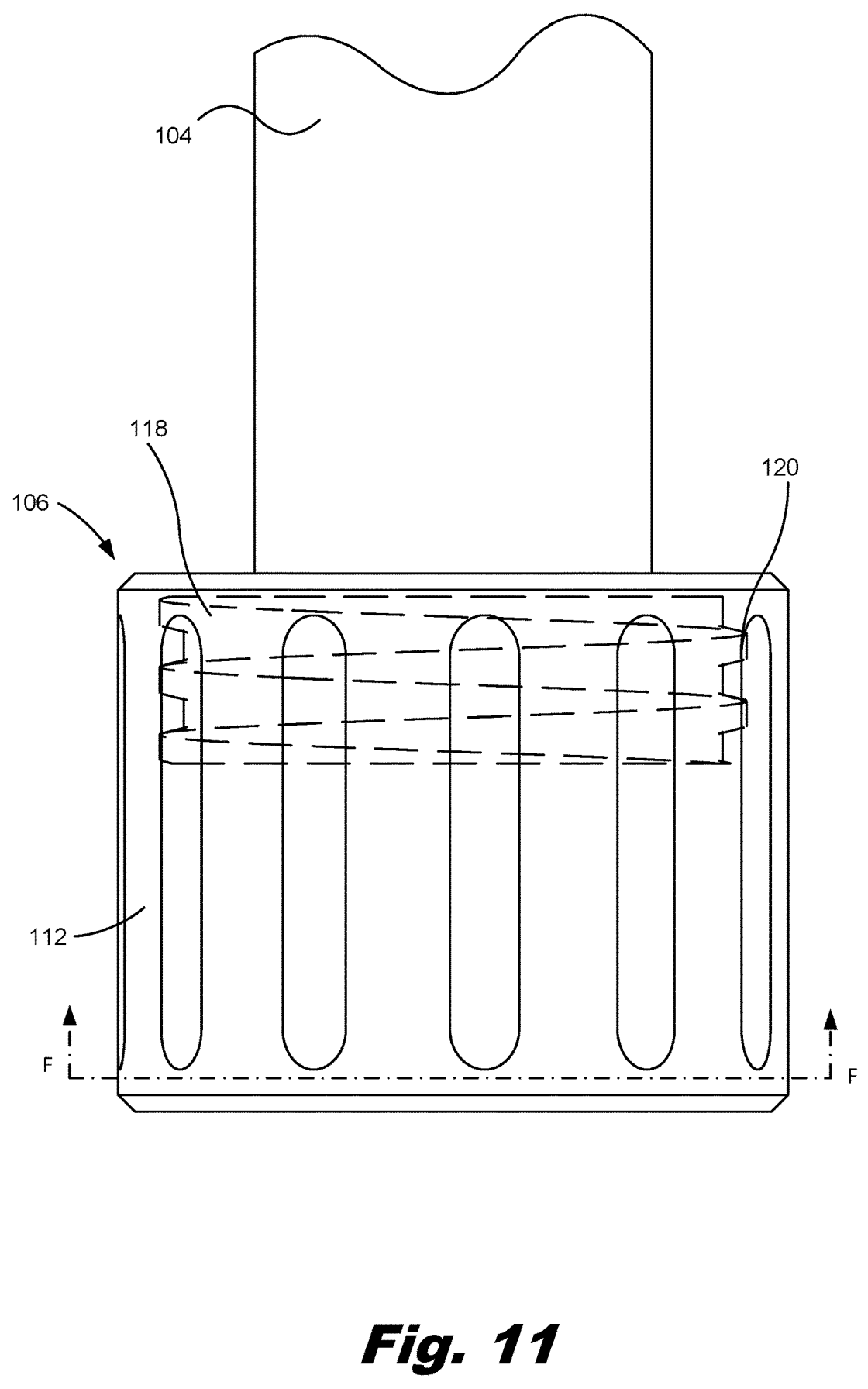

FIG. 11 is a graphic diagram front view of a rotatable barrel with a retaining ring formed in a retaining ring slot in the rotatable barrel, the upper pylon/proximate shaft portion, and the threaded sleeve of the prosthetic coupling device according to another embodiment of the present disclosure. Similar to FIG. 8, FIG. 11 shows the threaded sleeve 118 in dashed lines to show the relative position of the threaded sleeve 118 within the rotatable barrel 112.

Again, the outer threads 120 of the threaded sleeve 118 (and the internal barrel threads of the rotatable barrel as described herein) may be right-handed threads that follows the right-hand grip rule. However, it is appreciated that in other embodiments, the direction of the outer threads 120 (and internal barrel threads) may have an opposite threaded direction known as the left-handed thread direction. The right-handedness of the outer threads 120 shown in FIG. 11 allows for the rotation of the rotatable barrel 112 clockwise (e.g., as viewed from above by the patient) to lock the detachable coupler (not shown) into the internal mount (not shown) and the rotation of the rotatable barrel 112 counter-clockwise (e.g., as viewed from above by the patient) to unlock the detachable coupler from the internal mount.

Figure 13:
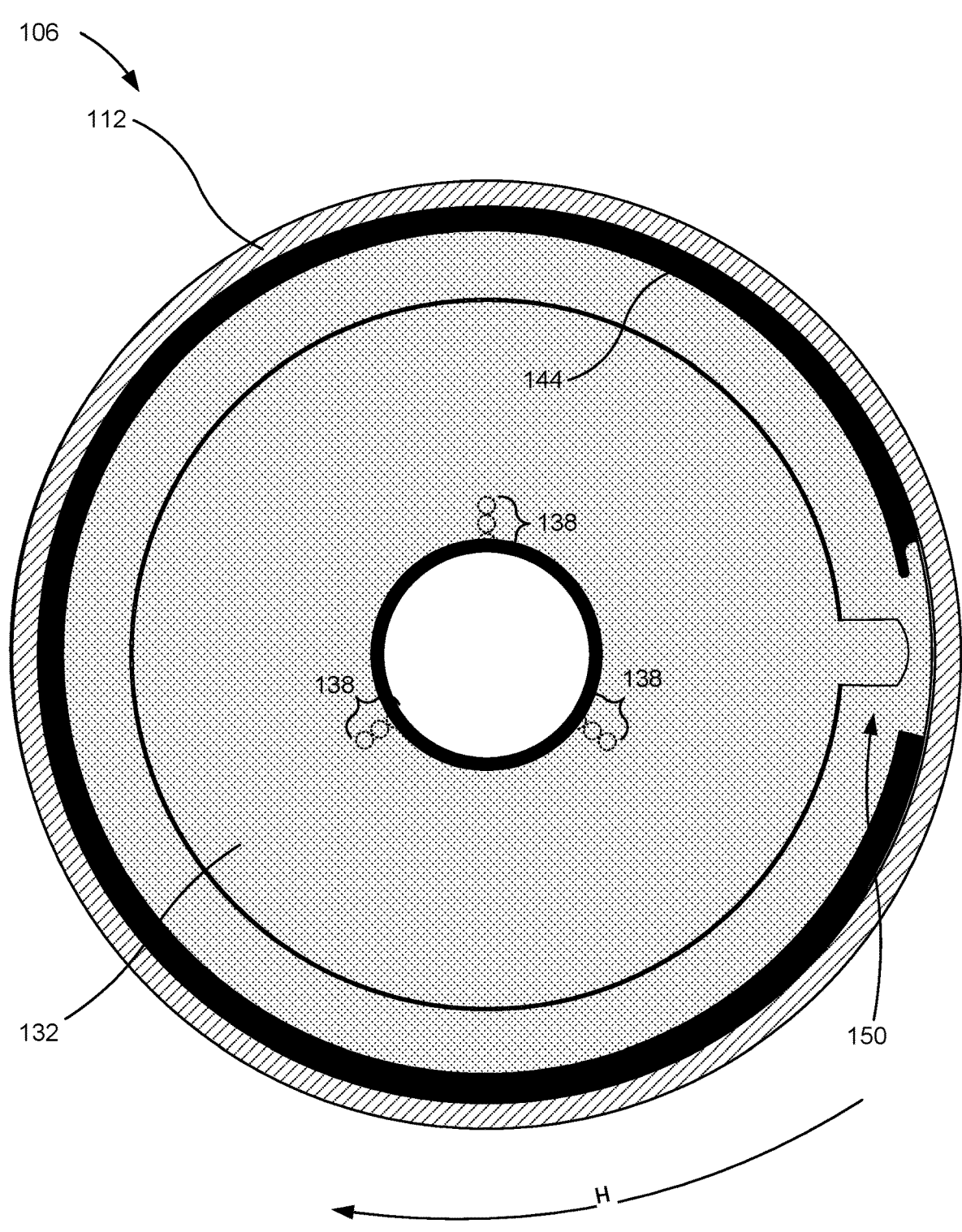
FIG. 13 is a graphic diagram bottom view of the rotatable barrel and internal mount of the prosthetic coupling device according to another embodiment of the present disclosure.

FIG. 11 also includes a section line "F" indicating a cross-sectional plane of the rotatable barrel 112 and shown in FIG. 12 and FIG. 13. FIG. 12 is a graphic diagram bottom view of the rotatable barrel 112 and internal mount 132 of the prosthetic coupling device according to another embodiment of the present disclosure. FIG. 13 is a graphic diagram bottom view of the rotatable barrel and internal mount of the prosthetic coupling device according to another embodiment of the present disclosure.

FIG. 12 shows the prosthetic coupling device 106 in a "locked" position without the detachable coupler present. As described herein, when the patient has rotated the rotatable barrel 112, the internal mount (not shown) fully engages a bottom interior side of the rotatable barrel 112. As the internal mount moves up towards the interior side of the rotatable barrel 112, the sloped face of the internal mount pushes the ball bearing set 138 through the horizontal ball bearing shaft causing a terminal ball bearing of the ball bearing set 138 to extend out from the necked portion of the horizontal ball bearing shaft 136. Again, because the horizontal ball bearing shaft has a necked portion, the terminal ball bearing of the ball bearing set 138 is prevented from exiting the horizontal ball bearing shaft completely.

As shown in FIG. 12, the patient has rotated the rotatable barrel 112 in a counterclockwise direction according to arrow "G." It is appreciated that the patient, when viewing the prosthetic coupling device 106 form above, the rotation of the rotatable barrel 112 in a clockwise direction causes the prosthetic coupling device 106 to be locked. The view presented in FIG. 12 is, however, from a bottom side of the prosthetic coupling device 106 such that the direction of rotation is described as a counterclockwise direction. It is appreciated, however, that the handedness of the outer threads 120 of the threaded sleeve 118 and the internal barrel threads 116 of the rotatable barrel 112 may be either a left-handedness or a right-handedness. FIGS. 1-12 describe the outer threads 120 and the internal barrel threads 116 as being right-handed threads. However, the internal barrel threads 116 and the outer threads 120 may be left-handed resulting in an opposite direction of rotation of the rotatable barrel 112 to lock the prosthetic coupling device 106 as described herein. The present specification contemplates this left-handed arrangement of the internal barrel threads 116 and the outer threads 120. However, for ease of understanding, the present specification describes the internal barrel threads 116 and the outer threads 120 as being right-handed.

FIG. 12 also shows a registering slot 150 formed into a portion of the internal mount 132. As described herein, the detachable coupler that mates with the internal mount 132 further includes, in an embodiment, a registering post (not shown) formed on an outside surface of the internal mount. The registering post is used by the patient to properly align the detachable coupler relative to the internal mount 132 of the prosthetic coupling device 106. In an embodiment, the registering post interfaces with this registering slot 150 formed into a bottom edge of the internal mount 132 of the prosthetic coupling device 106. This alignment of the detachable coupler relative to the internal mount 132 prevents the patient from misaligning the lower pylon and foot (or another prosthetic terminal device) relative to the upper pylon described in FIG. 1. Once aligned, the patient may lock the detachable coupler to the internal mount 132 of the prosthetic coupling device 106 as described herein (e.g., rotating the rotatable barrel 112) in order to be able place weight on the prosthetic coupling device 106/prosthetic device and walk properly using the prosthetic device.

FIG. 13 shows the prosthetic coupling device 106 in an unlocked orientation. Again, as described herein, the patient may rotate the rotatable barrel 112 in the direction of arrow "H" in order to unlock the prosthetic coupling device 106. This direction, as viewed in the bottom view shown in FIG. 13 is a clockwise direction. However, from the perspective of the patient, this rotational direction is a counterclockwise direction because the patient would be viewing the prosthetic coupling device 106 from above.

Both FIGS. 12 and 13 show the retaining ring 144 that has been placed in the retaining ring slot (not shown) formed on the rotatable barrel 112. The placement of the retaining ring 144 and formation of the retaining ring slot may be based on the length of the internal mount 132 such that the retaining ring slot is formed below the lowest end of the internal mount 132. The retaining ring 144, in an embodiment, prevents the rotatable barrel 112 from being removable by the patient during operation. During manipulation of the prosthetic coupling device 106 by the patient, the patient may rotate the threaded sleeve 118 counterclockwise (e.g., when the patient is unlocking the detachable coupler from the internal mount 132) causes the rotatable barrel 112 to move upwards. This movement of the rotatable barrel 112 upwards causes the lowest portion of the internal mount 132 to abut the retaining ring 144 preventing the complete removal of the rotatable barrel 112 from the prosthetic coupling device 106. Additionally, by preventing the removal of the rotatable barrel 112 from the internal mount 132 and threaded sleeve 118 by the retaining ring 144, the spring and tactile ball bearing are kept in place.

Figure 14:
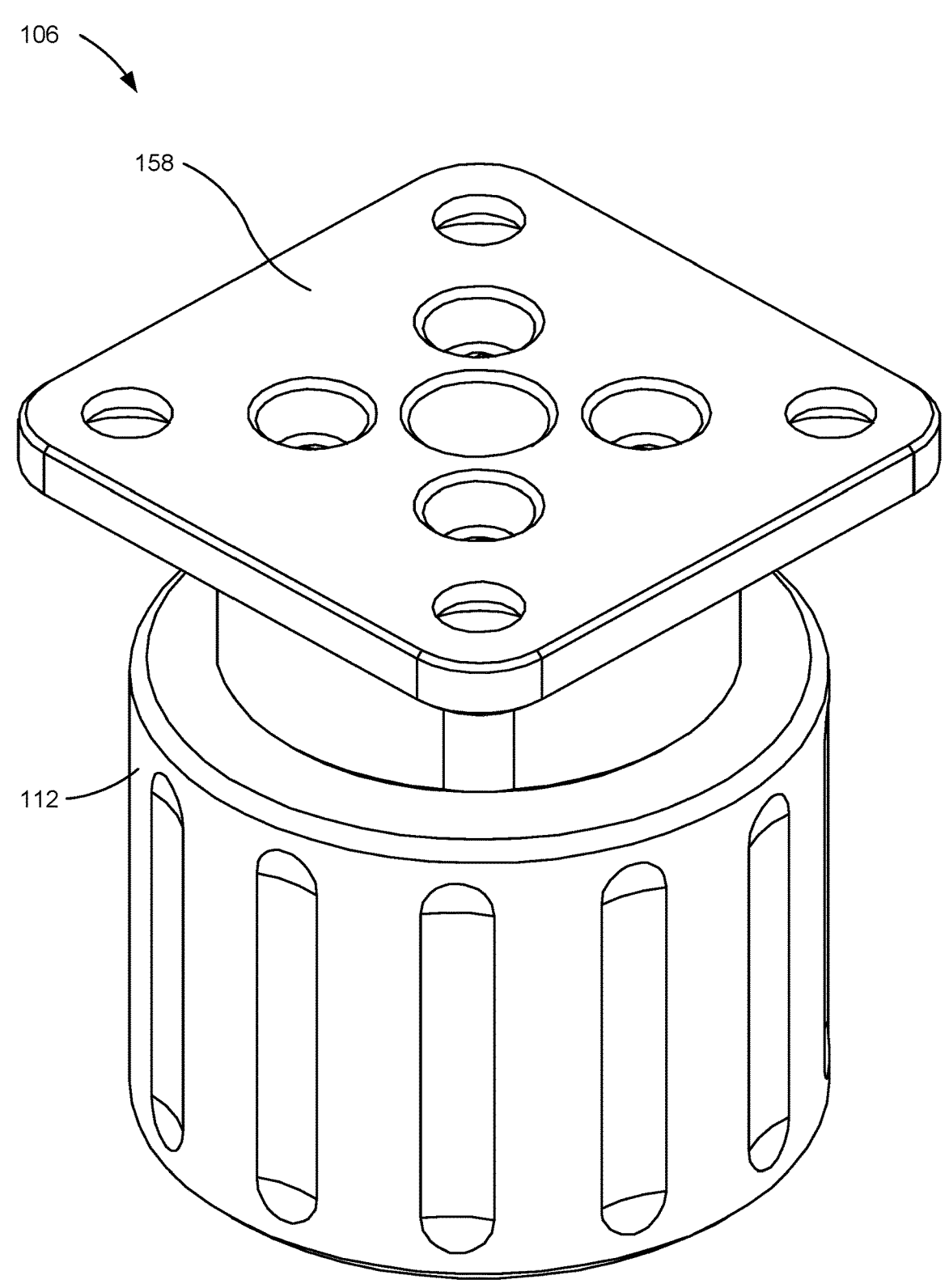
FIG. 14 is a perspective view of a prosthetic coupling device according to another embodiment of the present disclosure.

FIG. 14 is a perspective view of a prosthetic coupling device 106 according to another embodiment of the present disclosure. The prosthetic coupling device 106 show in FIG. 14 includes a socket coupler 158 operatively coupled to the internal mount 132 of the prosthetic coupling device 106. The socket coupler 158 may include a surface onto which other components of the prosthetic device (e.g., FIG. 1, 100) may be coupled to. In an embodiment, the socket coupler 158 is operatively coupled directly to a socket (e.g., FIG. 1, 102) of the prosthetic device. It is appreciated, however, that the socket coupler 158 may be used to be operatively coupled to other components of a prosthetic device. For example, the socket coupler 158 may be operatively coupled to a fixture directly implanted into a bone of a patient such as a femur bone. In this example embodiment, the socket coupler 158 may be operatively coupled to an abutment screw or other coupling device formed at a terminal end the fixture implanted into the patient's bone.

Similar to FIG. 4, FIG. 14 shows the rotatable barrel 112 rotatable in a counterclockwise direction, in an example embodiment, that causes the detachable coupler (not shown) to be removed from the prosthetic coupling device 106. Additionally, as described herein, the internal mount abuts the retaining ring (not shown) as a result of the internal barrel threads (not shown) of the rotatable barrel (not shown) and the outer threads (not shown) of the threaded sleeve (not shown) being unthreaded as described in connection with FIG. 3, for example.

Figure 15:
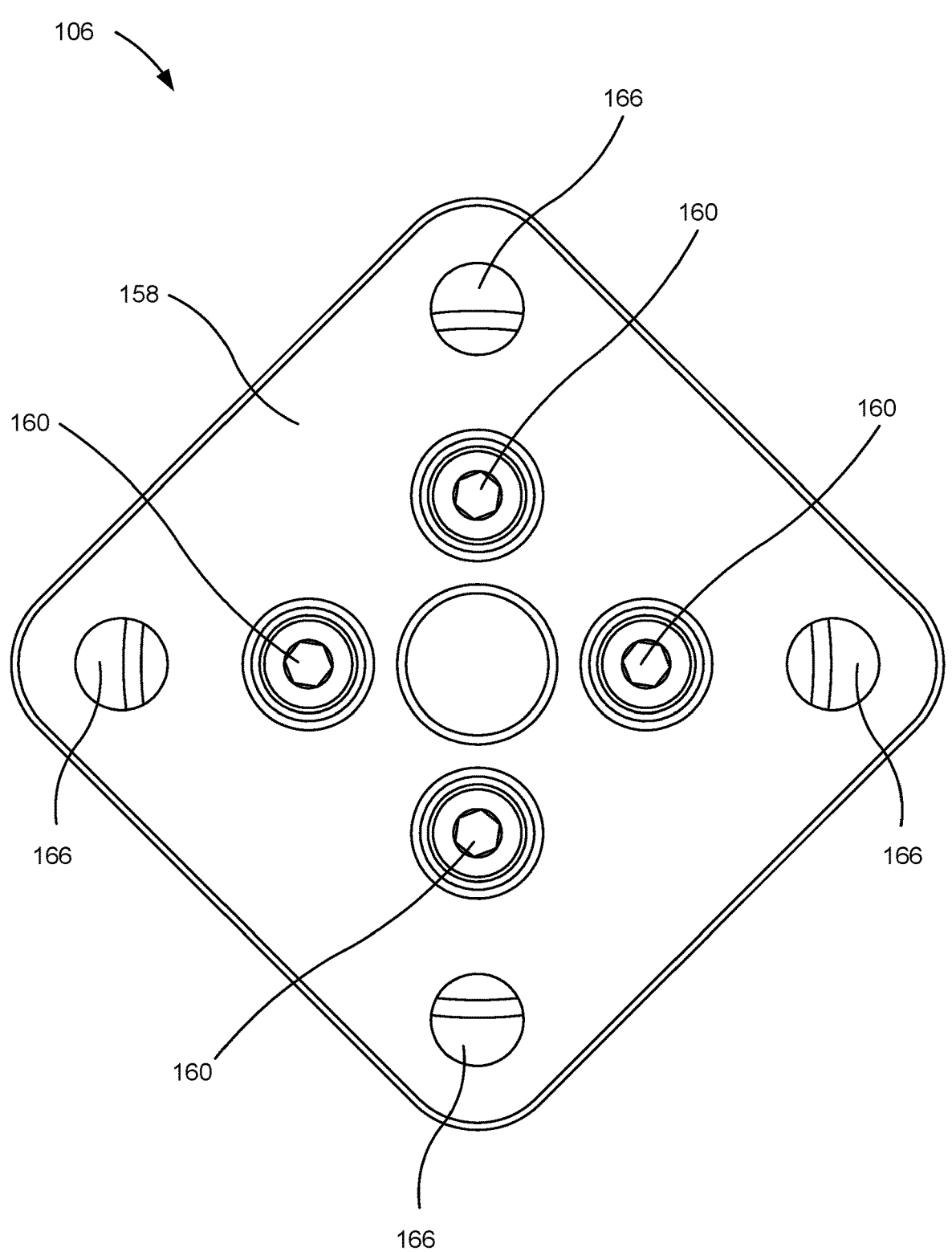
FIG. 15 is a top view of a prosthetic coupling device according to another embodiment of the present disclosure.

Further details of the socket coupler 158 are shown in FIG. 15. FIG. 15 is a top view of the prosthetic coupling device 106 that includes a socket coupler 158 according to another embodiment of the present disclosure. This top view of the prosthetic coupling device 106 and the socket coupler 158 shows that the socket couple is operatively coupled to the internal mount (not shown) via as set of socket coupler bolts 160. In the example embodiment shown in FIG. 15, four socket coupler bolts 160 is used to secure the socket coupler 158 to the internal mount and the remaining portions of the prosthetic coupling device 106. The socket coupler bolts 160 may include any diameter of bolts (e.g., either major diameter or minor diameter) that may be passed into socket coupler bolt vias (not shown) formed into a lip of the internal mount.

In the embodiment shown in FIG. 15, the socket coupler 158 includes one or more socket coupler coupling holes 166 used to operatively couple the socket coupler 158 and the remaining portions of the prosthetic coupling device 106 to a socket or other device of the prosthetic device. In an embodiment, the socket coupler coupling holes 166 may be threaded to receive a bolt or screw used to couple the socket coupler 158 to these other portions of the prosthetic device described herein. Additionally or alternatively, the socket coupler coupling holes 166 may be positioned such that a nut associated with those bolts or other fasteners may be used to secure the socket coupler 158 to the other components or devices of the prosthetic device as described herein. For example, the socket coupler bolts 160 may be used to secure the socket coupler 158 to a socket (e.g., FIG. 1, 102) or other components such as a vacuum pump used to create a vacuum between a liner around a patient's leg and a socket wall. In an embodiment, the socket coupler coupling holes 166 may receive countersunk screws that, when fully seated into the socket coupler 158 to couple the socket coupler 158 to another component of the prosthetic device, is flat along a surface of the socket coupler 158. It is appreciated that other coupling devices apart from or an in addition to the socket coupler coupling holes 166 may be used to couple the socket coupler 158 to a socket or other component of the prosthetic device and the present specification contemplates those other coupling devices.

Figure 16:
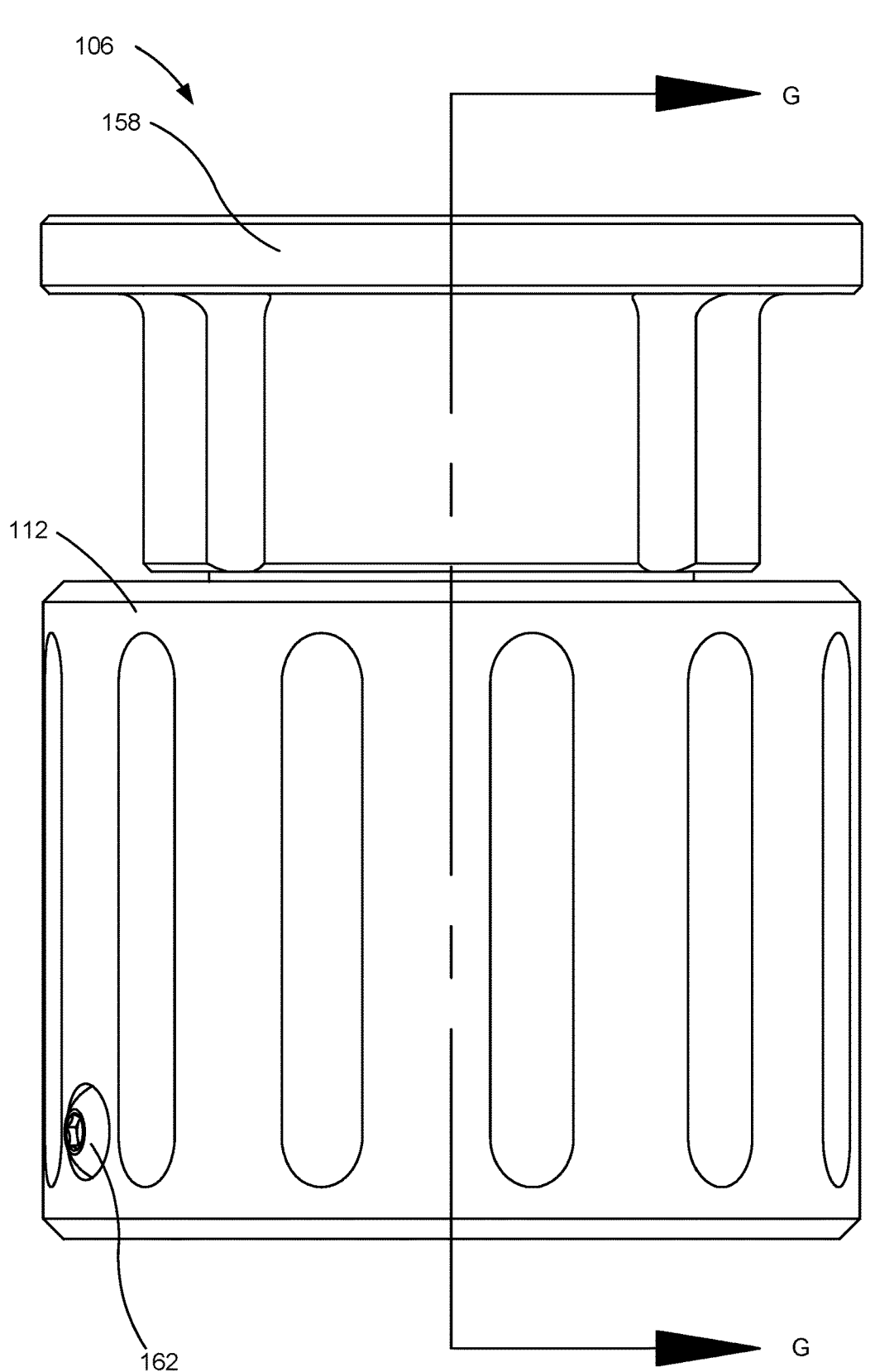
FIG. 16 is a side view of a prosthetic coupling device according to another embodiment of the present disclosure.
Figure 17:
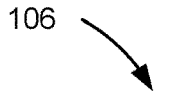
FIG. 17 is a side, cross-section view of a prosthetic coupling device according to another embodiment of the present disclosure.

FIGS. 16 and 17 show further details of the socket coupler 158, the socket coupler bolts 160, and the socket coupler bolt vias 168 described herein. FIG. 16 is a side view of a prosthetic coupling device 106 showing the socket coupler 158 operatively coupled to the internal mount (not shown) of the prosthetic coupling device 106 according to another embodiment of the present disclosure. Additionally, FIG. 17 is a side, cross-section view of a prosthetic coupling device according to another embodiment of the present disclosure. FIG. 16 also includes a section line "G" indicating a cross-sectional plane of the prosthetic coupling device 106 with the socket coupler 158 shown in FIG. 17 and FIG. 13.

As shown in FIG. 16, the socket coupler 158 may be generally flat to interface with a relatively flat surface of a component of the prosthetic device to which the prosthetic coupling device 106 is to be coupled to. It is appreciated, however, that the surface of the socket coupler 158 may fit with other portions of those potential components of the prosthetic device and may include surfaces that increase a coefficient of friction or provide additional engineering fits between the socket coupler 158 and these other components of the prosthetic device.

FIG. 16 further shows a rotational set screw 162 formed into and through the rotatable barrel 112 of the prosthetic coupling device 106. As described herein, the rotational set screw 162 may extend through the rotatable barrel 112 and into a set screw channel (not show in FIG. 16). The interaction between the rotational set screw 162 and the set screw channel may, in example embodiments described herein, prevent over rotation of the rotatable barrel 112 in either the clockwise direction of rotation or the counterclockwise direction of rotation. The interaction between the rotational set screw 162 and the set screw channel may, therefor, prevent locking of the rotatable barrel 112 relative to the threaded sleeve 118 by the user as the user rotates the rotatable barrel 112 in either the clockwise or counterclockwise direction. The set screw channel is shown in more detail in FIGS. 17, 20-22, and FIG. 24.

Turning to FIG. 17, the cross-section side view of the prosthetic coupling device 106 is along section line "G" shown in FIG. 16. This cross-section view shows the socket coupler 158 operatively coupled to the internal mount 132 of the prosthetic coupling device 106. As described herein, the socket coupler 158 is operatively coupled to the internal mount 132 via one or more socket coupler bolts 160. The socket coupler bolts 160 may be passed through and into one or more socket coupler bolt vias 168 formed into a lip portion of the internal mount 132. In an embodiment, the socket coupler bolt vias 168 may be threaded to receive threads from each of the socket coupler bolts 160. A thickness of the internal mount may exceed the diameter of the socket coupler bolts 160 (e.g., either major diameter or minor diameter)) such that the socket coupler bolts 160 can be seated into the internal mount 132 without the structural integrity of the internal mount 132 as weight is placed on these components.

FIG. 17 also shows a set screw channel 164 into which the rotational set screw (not shown) may extend into the prosthetic coupling device 106. This set screw channel 164 may be formed along an outer surface of the internal mount 132 and may extend, radially, a length along this outer surface of the internal mount 132. As described herein, the retaining ring 144, in an embodiment, prevents the rotatable barrel 112 from being removable by the patient during operation in an embodiment. However, during operation the user may rotate the rotatable barrel 112 to decouple or couple the internal mount 132 from or to the detachable coupler 140. The user may inadvertently over-rotate the rotatable barrel 112 causing the components of the prosthetic coupling device 106 to be torqued against one another (e.g., the rotatable barrel 112 to the threaded sleeve 118, the internal mount 132 against the retaining ring 144, etc.). The inclusion of the rotational set screw 162 and the set screw channel 164 as well as the length of the set screw channel 164 prevents this over-torquing of these components against each other even where the user uses significant force to rotate the rotatable barrel 112 to uncouple or couple the detachable coupler 140 from or to the other components of the prosthetic coupling device 106 (e.g., the internal mount 132).

Figure 18:
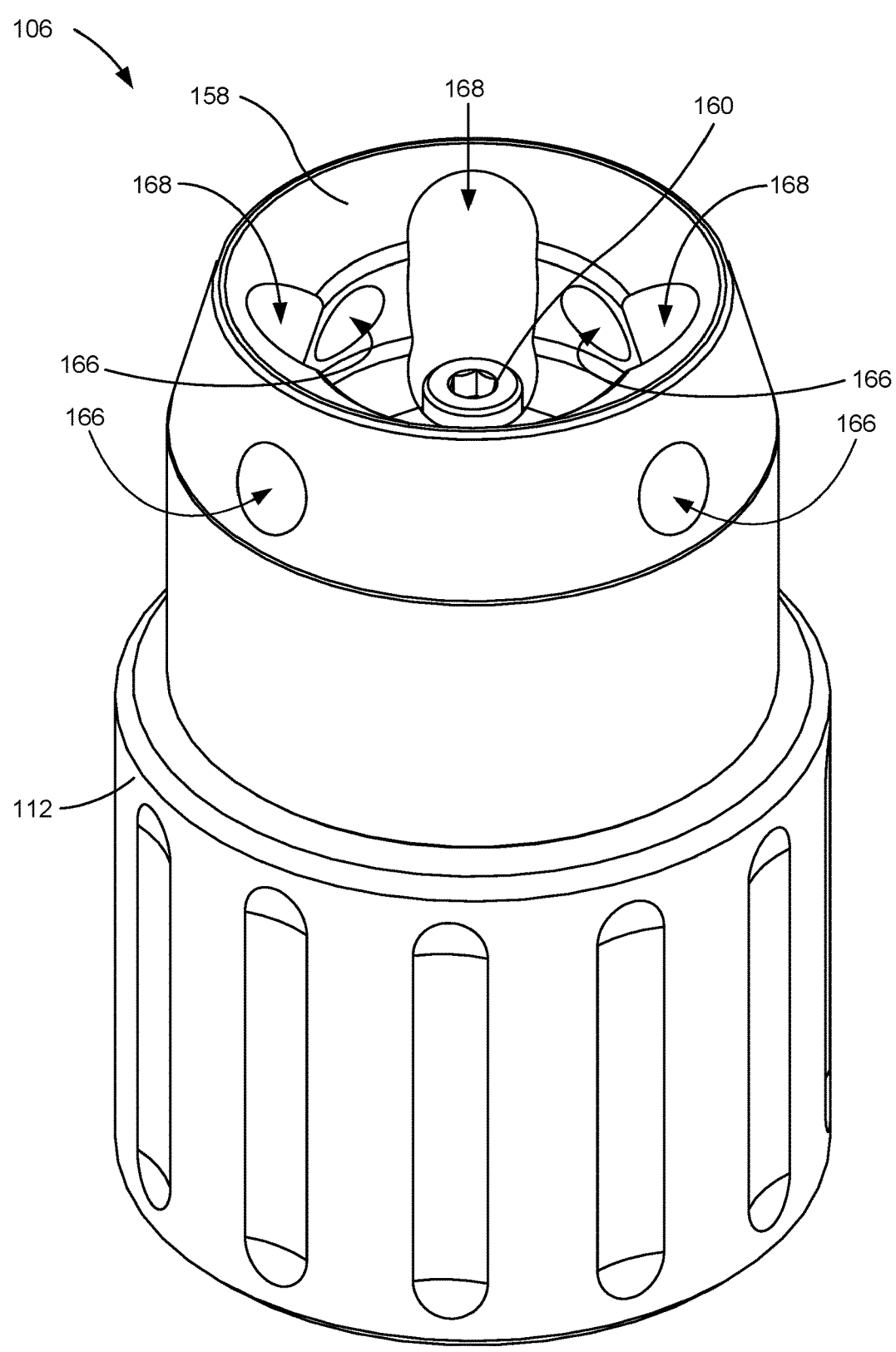
FIG. 18 is a perspective view of a prosthetic coupling device according to another embodiment of the present disclosure.
Figure 19:
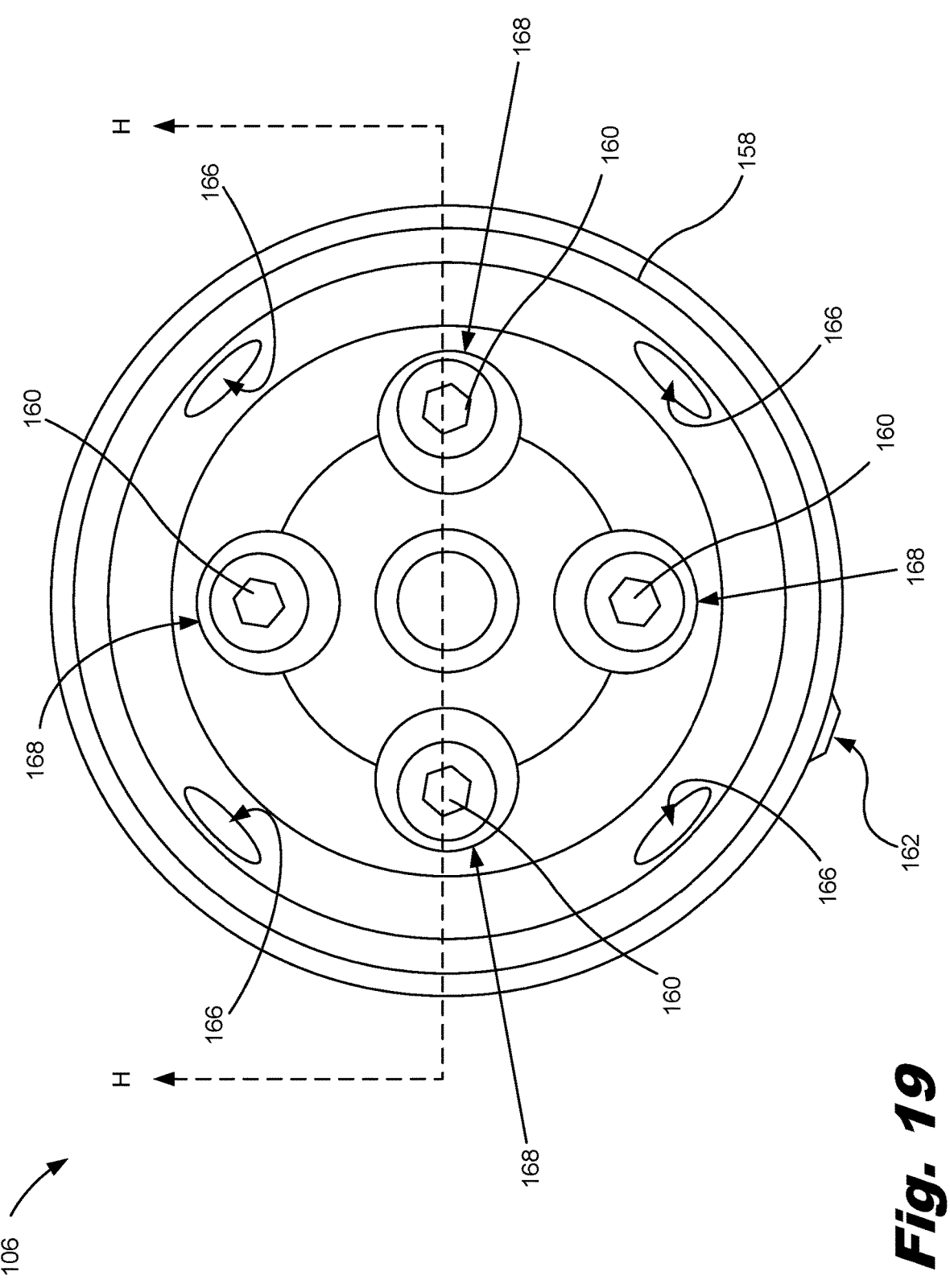
FIG. 19 is a top view of a prosthetic coupling device according to another embodiment of the present disclosure.
Figure 20:
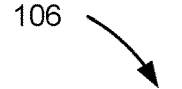
FIG. 20 is a side, cross-section view of a prosthetic coupling device according to another embodiment of the present disclosure.

FIGS. 18, 19, and 20 show another example embodiment, of a socket coupler 158 that allows the prosthetic coupling device 106 to be interfaced with other components of the prosthetic device as described herein. FIG. 18 is a perspective view of a prosthetic coupling device 106 according to another embodiment of the present disclosure. Further, FIG.

19 is a top view of a prosthetic coupling device 106 according to another embodiment of the present disclosure. Still further, FIG. 20 is a side, cross-section view of a prosthetic coupling device 106 according to another embodiment of the present disclosure. The prosthetic coupling device 106 shown in FIGS. 18-20 include a socket coupler 158. The socket coupler 158 may be in a different form than that shown in, for example, FIGS. 14-17 and may be used to secure the prosthetic coupling device 106 to different types of prosthetic devices. The socket coupler 158 shown in FIG. 18 may be a female pyramid coupler used to couple the prosthetic coupling device 106 to a pyramid-style terminator on a prosthetic device (e.g., FIG. 1, 100). In an embodiment, the socket coupler 158 also includes one or more socket coupler bolts 160 put into one or more socket coupler bolt vias 168 in order to secure the socket coupler 158 to the internal mount 132 of the prosthetic coupling device 106. In an embodiment, offset counterbores may be formed into the prosthetic coupling device 106 to create the socket coupler bolt vias 168 on the socket coupler 158 so that a facilitating relief may be created for angle adjustment on the pyramid-style terminator on a prosthetic device (e.g., FIG. 1, 100).

Similar to FIGS. 15 and 17, the socket coupler 158 of FIG. 18 includes one or more socket coupler coupling holes 166 used to secure the pyramid-style terminator on a prosthetic device (e.g., FIG. 1, 100), for example, to the socket coupler 158 when the prosthetic coupling device 106 is coupled to the prosthetic device. In the example embodiment shown in FIG. 18, the socket coupler coupling holes 166 may be used to pass a bolt or other securing device through the socket coupler 158, into a central location of the socket coupler 158, and against the pyramid-style terminator on a prosthetic device or other coupling device that the socket coupler 158 may be coupled to.

Turning to FIG. 19, the socket coupler 158 includes, in an embodiment, four socket coupler bolts 160 each placed within a socket coupler bolt via 168. Similar to FIGS. 14, 15, and 17, the socket coupler bolt vias 168 may pass through the socket coupler 158 and into a lip of the internal mount 132. It is appreciated that more or less than four socket coupler bolts 160 and socket coupler bolt vias 168 may be used to couple the socket coupler 158 to the internal mount 132 and the present specification contemplates the use of more or less than the four socket coupler bolts 160 shown in FIG. 19. The socket coupler 158 further includes four socket coupler coupling holes 166 used to secure the socket coupler 158 to terminal ends of the prosthetic device (e.g., FIG. 1, 100). Additionally, the present specification contemplates the use of more or less than the four socket coupler coupling holes 166 shown in FIG. 19 in order to secure a terminal end coupler on a prosthetic device to the socket coupler 158.

FIG. 19 also includes a section line "H" indicating a cross-sectional plane of the prosthetic coupling device 106 and is shown in FIG. 20. This cross-section view in FIG. 20 shows the socket coupler 158 operatively coupled to the internal mount 132 of the prosthetic coupling device 106. As described herein, the socket coupler 158 is operatively coupled to the internal mount 132 via one or more socket coupler bolts 160. The socket coupler bolts 160 may be passed through and into one or more socket coupler bolt vias 168 formed into a lip portion of the internal mount 132. In an embodiment, the socket coupler bolt vias 168 may be threaded to receive threads from each of the socket coupler bolts 160. A thickness of the internal mount may exceed the diameter of the socket coupler bolts 160 (e.g., either major diameter or minor diameter)) such that the socket coupler bolts 160 can be seated into the internal mount 132 without the structural integrity of the internal mount 132 as weight is placed on these components.

FIG. 20 also shows a set screw channel 164 into which the rotational set screw (not shown) may extend into the prosthetic coupling device 106. This set screw channel 164 may be formed along an outer surface of the internal mount 132 and may extend, radially, a length along this outer surface of the internal mount 132. As described herein, the retaining ring 144, in an embodiment, prevents the rotatable barrel 112 from being removable by the patient during operation in an embodiment. However, during operation the user may rotate the rotatable barrel 112 to decouple or couple the internal mount 132 from or to the detachable coupler 140. Again, during operation, the user may inadvertently over-rotate the rotatable barrel 112 causing the components of the prosthetic coupling device 106 to be torqued against one another (e.g., the rotatable barrel 112 to the threaded sleeve 118, the internal mount 132 against the retaining ring 144, etc.). The inclusion of the rotational set screw 162 and the set screw channel 164 as well as the length of the set screw channel 164 prevents this over-torquing of these components against each other even where the user uses significant force to rotate the rotatable barrel 112 to uncouple or couple the detachable coupler 140 from or to the other components of the prosthetic coupling device 106 (e.g., the internal mount 132).

Figure 21:
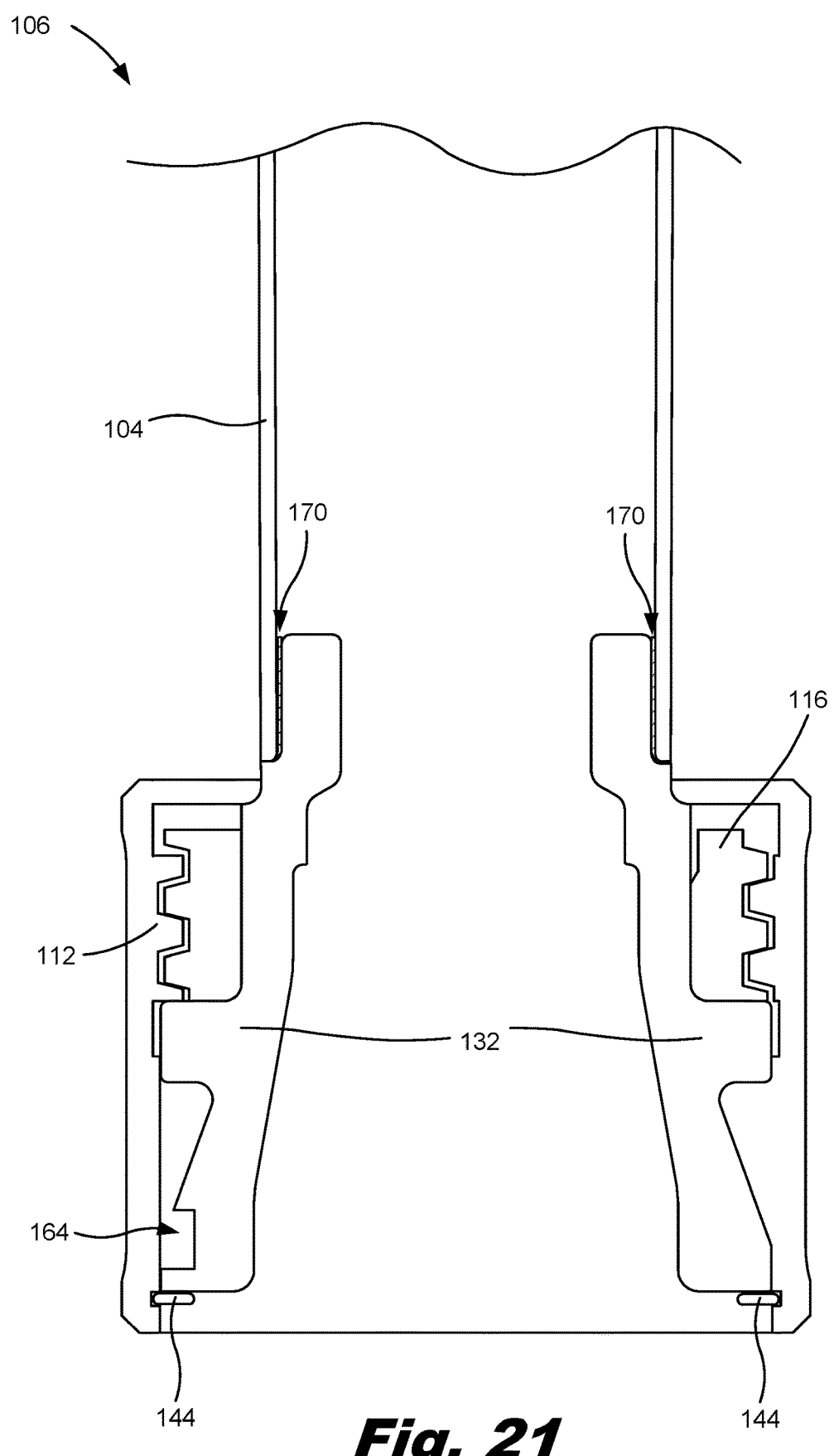
FIG. 21 is a side, cross-section view of a prosthetic coupling device according to another embodiment of the present disclosure.

FIG. 21 is a side, cross-section view of a prosthetic coupling device 106 according to another embodiment of the present disclosure. The cross-section view of the prosthetic coupling device 106 may be similar to the cross-section view shown in FIG. 5 except, in FIG. 21, the internal mount 132 is coupled to an upper pylon 104 or other component of the prosthetic device. In FIG. 21, the internal mount 132 may have an upper portion that has a smaller outer diameter than an internal diameter of the upper pylon 104. This allows the upper pylon 104 to be placed around the upper portion of the internal mount 132 for the upper pylon 104 to be secured to the internal mount 132 of the prosthetic coupling device 106. In an embodiment, the upper pylon 104 may be pressed fit onto the upper portion of the internal mount 132 with the interface between the upper pylon 104 and the upper portion of the internal mount 132 being a press fit, a driving fit, or a forced fit among other types of engineering fits.

In the embodiment shown in FIG. 21, the upper pylon 104 may be operatively coupled to an upper portion of the internal mount 132 via application of a glue 170. This glue 170 may be applied to those surfaces where the interior surface of the upper pylon 104 interfaces with the exterior surface of the upper portion of the internal mount 132. As described herein, an industrial glue may be used to secure the upper pylon 104 to the upper portion of the internal mount 132. An example of an industrial glue that can be used to couple one or more components of the prosthetic coupling device 106 together may include 3M® Scotch-Weld® epoxy adhesive DP420 or DP 420NS or similar types of glues, epoxy, or chemical adhesives. Scotch-Weld® is a registered trademark of the 3M corporation of Maplewood, Minnesota. This glue 170 may bond the upper pylon 104 to the upper portion of the internal mount 132 to an extent to allow the user to place weight onto the interface between the upper pylon 104 and the internal mount 132. In an embodiment where the prosthetic device is a leg prosthetic as shown in FIG. 1, for example, the entire user's weight may be placed on the interface between the upper pylon 104 and the internal mount 132 as shown in FIG. 21 without the upper pylon 104 breaking away from the internal mount 132.

FIG. 22 is a side view of an internal mount 132 of a prosthetic coupling device (e.g., FIG. 1, 106) according to another embodiment of the present disclosure. In the embodiment shown in FIG. 22, the internal mount 132 has had the threaded sleeve, the ball bearing set, the spring, the tactile ball bearing, rotatable barrel 112, and the screw have all been removed to show the internal mount 132 without these components. However, the socket coupler bolt vias 168 formed in the lip of the internal mount 132 and the horizontal ball bearing shaft 136 are shown in FIG. 22.

FIG. 22 further shows the set screw channel 164 formed into the detachable coupler 140. The set screw channel 164 may be formed on a lower portion of the internal mount 132 or placed in a location where the functions of the rotational set screw (not shown) relative to the set screw channel 164 are not interfering with the operations of the other components of the prosthetic coupling device 106 described herein. Again, during operation, the user may inadvertently over-rotate the rotatable barrel (not shown) causing the components of the prosthetic coupling device 106 to be torqued against one another (e.g., the rotatable barrel to the threaded sleeve, the internal mount against the retaining ring, etc.). The inclusion of the rotational set screw and the set screw channel 164 as well as the length of the set screw channel 164 prevents this over-torquing of these components against each other even where the user uses significant force to rotate the rotatable barrel to uncouple or couple the detachable coupler (not shown) from or to the other components of the prosthetic coupling device 106 (e.g., the internal mount 132).

Figure 23:
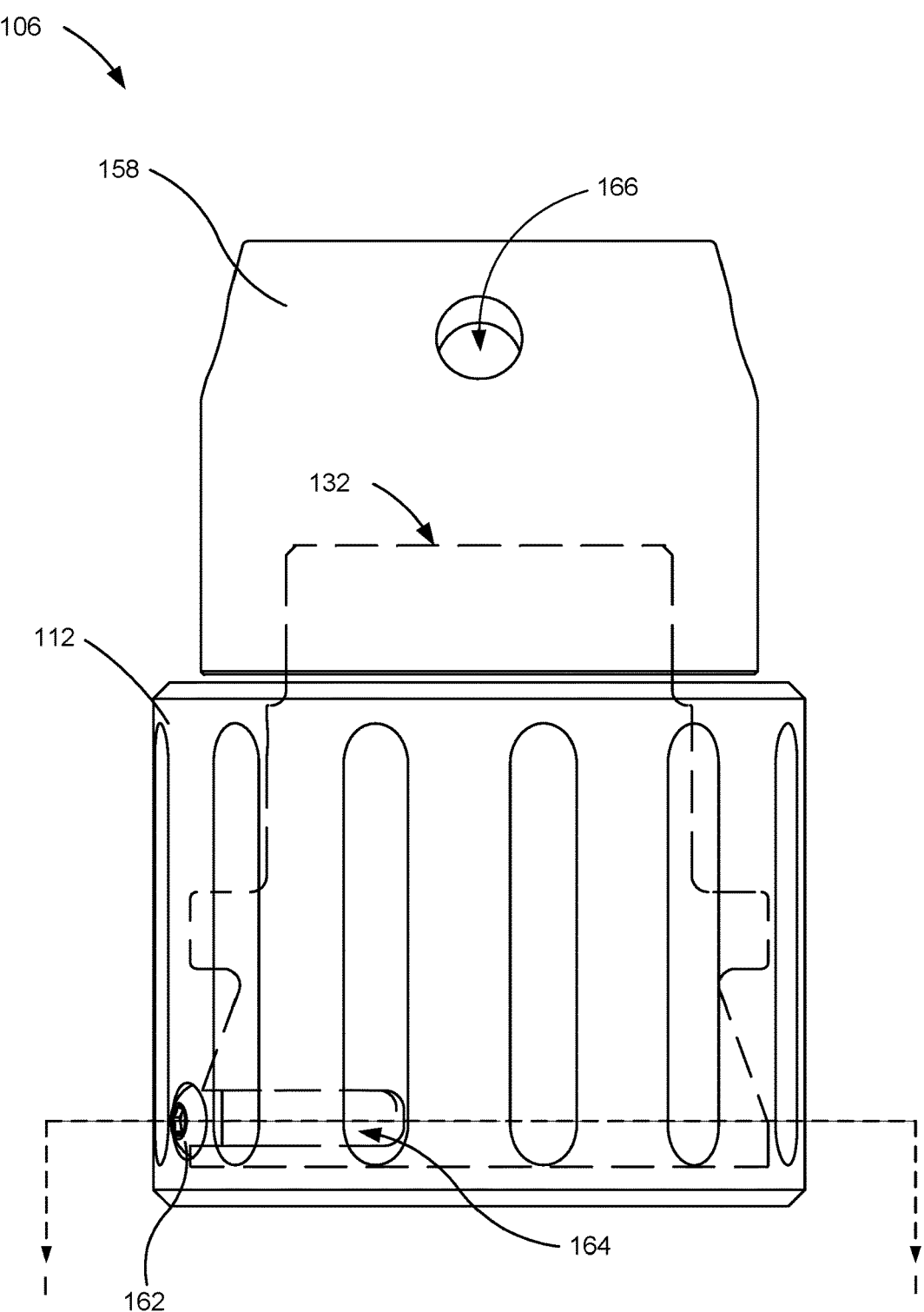
FIG. 23 is a graphic diagram side view of the prosthetic coupling device including a rotatable barrel and internal mount according to another embodiment of the present disclosure.
Figure 24:
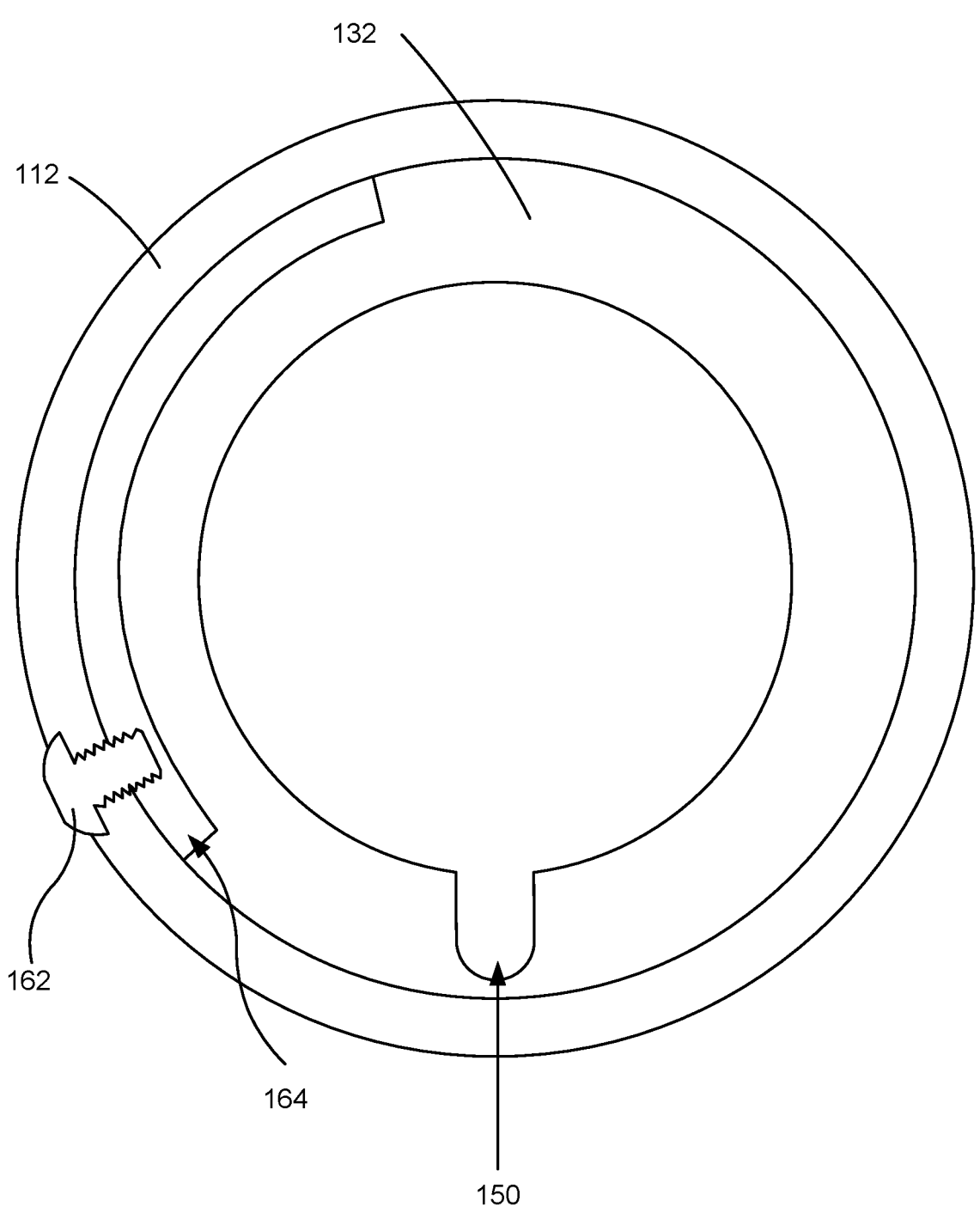
FIG. 24 is a graphic diagram bottom view of the prosthetic coupling device including a rotatable barrel and internal mount according to another embodiment of the present disclosure.

FIGS. 23 and 24 show the interface between the rotational set screw 162 and the set screw channel 164 in an embodiment. FIG. 23 is a graphic diagram side view of the prosthetic coupling device 106 including a rotatable barrel 112 and internal mount 132 according to another embodiment of the present disclosure. FIG. 23 shows the internal mount 132 as week as the set screw channel 164 in dashed lines to show their relative position within the prosthetic coupling device 106. Further FIG. 23 shows a similar socket coupler 158 with its socket coupler coupling holes 166 as that shown in FIGS. 18-20. FIG. 24 is a graphic diagram bottom view of the prosthetic coupling device 106 including a rotatable barrel 112 and internal mount 132 according to another embodiment of the present disclosure along section line "I" of FIG. 23.

FIG. 23 again shows the relative position of the set screw channel 164 to the rotational set screw 162. In an embodiment, the set screw channel 164 may be formed along an outer surface of the internal mount 132 and may extend, radially, a length along this outer surface of the internal mount 132. As described herein, the retaining ring (not shown), in an embodiment, prevents the rotatable barrel 112 from being removable by the patient during operation in an embodiment. Again, the user may inadvertently over-rotate the rotatable barrel 112 causing the components of the prosthetic coupling device 106 to be torqued against one another (e.g., the rotatable barrel 112 to the threaded sleeve (not shown), the internal mount 132 against the retaining ring (not shown), etc.). The inclusion of the rotational set screw 162 and the set screw channel 164 as well as the length of the set screw channel 164 prevents this over-torquing of these components against each other even where the user uses significant force to rotate the rotatable barrel 112 to uncouple or couple the detachable coupler 140 from or to the other components of the prosthetic coupling device 106 (e.g., the internal mount 132).

FIG. 24 shows the rotational set screw 162 placed through the rotatable barrel 112 and into the space formed by the set screw channel 164. In an embodiment, the rotational set screw 162 may include threads that allow the rotational set screw 162 to remain in place relative to the rotational barrel 112 during use of the prosthetic coupling device 106. As shown in FIG. 24, a length of the rotational set screw 162 passes a distance into the set screw channel 164 such that, when the rotatable barrel 112 is rotated relative to the internal mount 132, terminal ends of the set screw channel 164 may prevent further rotation of the rotatable barrel 112 relative to the internal mount 132. Again, this prevents over-rotation of the rotatable barrel 112 relative to the internal mount 132 thereby preventing the torquing of the components of the prosthetic coupling device 106 against each other (e.g., the rotatable barrel 112 to the threaded sleeve (not shown), the internal mount 132 against the retaining ring (not shown), etc.) as described herein.

FIG. 24 also shows a registering slot 150 formed into a portion of the internal mount 132. As described herein, the detachable coupler (not shown) that mates with the internal mount 132 further includes, in an embodiment, a registering post (not shown) formed on an outside surface of the internal mount 132. The registering post is used by the patient to properly align the detachable coupler relative to the internal mount 132 of the prosthetic coupling device 106. In an embodiment, the registering post interfaces with this registering slot 150 formed into a bottom edge of the internal mount 132 of the prosthetic coupling device 106. This alignment of the detachable coupler relative to the internal mount 132 prevents the patient from misaligning the lower pylon and foot (or another prosthetic terminal device) relative to the upper pylon described in FIG. 1 for example or otherwise allows for proper alignment of the components of the prosthetic device described herein.

FIG. 25 is a flow diagram of a method 2500 of manufacturing a prosthetic device according to an embodiment of the present disclosure. The method 2500 described herein may include, at block 2505, placing a threaded sleeve around an internal mount. In an embodiment, an upper pylon may form a monolithic piece with the internal mount requiring the threaded sleeve to be slid down the upper pylon until the threaded sleeve rests on a shelf formed onto the internal mount. At this point, the threaded sleeve may not be secured to the shelf formed onto the internal mount so that other components of the prosthetic coupling device may be assembled.

At block 2510, a ball bearing set may be placed into a horizontal ball bearing shaft formed through the internal mount via a ball bearing channel. As described herein, the ball bearing channel is formed into the threaded sleeve so that the assembly process of the prosthetic coupling device may be conducted easier. The ball bearing channels may be used to guide each of the ball bearings into their respective horizontal ball bearing shafts during assembly. During the assembly process, in an example embodiment, the ball bearing channels may be aligned with their respective horizontal ball bearing shafts prior to the screws being inserted into their screw vias to secure the threaded sleeve to the shelf of the internal mount. When the ball bearing channels are aligned with their respective horizontal ball bearing shafts, a manufacturer or assembler may direct the ball bearing sets to be inserted into their respective horizontal ball bearing shafts. Again, the present specification contemplates the use of any number of ball bearings having any radius to form the ball bearing set with varying diameters of the horizontal ball bearing shaft to accommodate those numbers of ball bearings with a specific radius as well as the thickness of the walls of the internal mount. Additionally, the number of ball bearing channels is equal to the number of horizontal ball bearing shafts formed through the internal mount.

Once the ball bearing sets have been inserted into their respective horizontal ball bearing shafts, the method 2500 includes, at block 2515, rotating the threaded sleeve such that a ball bearing set barrier formed into the threaded sleeve prevents the ball bearings of the ball bearing sets from exiting the horizontal ball bearing shaft at a terminal end closest to the rotatable barrel. Similar to this arrangement shown in FIG. 9, for example, the threaded sleeve is rotated clockwise in order to place the ball bearing set barrier behind the ball bearing sets. It is appreciated that the arrangement of the ball bearing channels and ball bearing set barriers would necessitate that the threaded sleeve is rotated counterclockwise direction to cause the ball bearing set barrier to abut the ball bearing sets and the present specification contemplates this other arrangement.

The method 2500 further includes, at block 2520, preventing the rotation of the threaded sleeve around the internal mount by placing a fastening device into a screw via formed into the threaded sleeve and into the shelf of the internal mount. As described herein, the fastening device is a screw. In an embodiment, the screw may be partially screwed into the shelf such that the threaded sleeve may move, vertically, a specific distance along the outer surface of the internal mount. A height of the screw head of the screw may be set such that a maximum vertical distance that the threaded sleeve is allowed to move is set.

As described herein, a spring and ball channel may be formed vertically into the threaded sleeve. The method 2500 includes placing a spring and tactile ball bearing into the spring and ball channel formed in the threaded sleeve at block 2525. In an embodiment, the tactile ball bearing, during operation of the prosthetic coupling device, engages with a plurality of interior barrel detents formed on an interior surface of a top end of the rotatable barrel. The tactile ball bearing is pressed against the interior surface of the rotatable barrel by the spring. The spring and ball channel is formed in a vertical direction so that a distal end of the spring may press against an interior lower wall of the spring and ball channel in order to also press the tactile ball bearing against the interior barrel detents of the rotatable barrel as described herein. In an embodiment, therefore, the spring is biased to force the tactile ball bearing against the interior surface of the rotatable barrel and into the plurality of interior barrel detents. The plurality of interior barrel detents may be formed along the interior surface of the rotatable barrel such that as the patient rotates the rotatable barrel during operation, the tactile ball bearing is forced out of a first interior barrel detent, rolled toward a second interior barrel detent, and is pressed into the second interior barrel detent providing tactile feedback to the patient. This process continues as the tactile ball bearing passes along the individual interior barrel detents providing tactile feedback to the patient. Additionally, the force imparted onto the tactile ball bearing and into the interior barrel detents by the spring may provide additional resistive force that prevents unintended or unwanted rotation of the rotatable barrel unless the patient is rotating the rotatable barrel. The rotative force the patient imparts on the rotatable barrel overcomes this resistive force imparted by the spring against the tactile ball bearing and interior barrel detents. The present specification contemplates that multiple spring and ball channels may be formed into the threaded sleeve.

At block 2530, the method 2500 includes operatively coupling the rotatable barrel to the internal mount by threading the threads of the threaded sleeve with threads formed on an interior surface of the rotatable barrel. The rotatable barrel includes a via through which the upper pylon and the internal mount may pass similar to the threaded sleeve described herein. As the internal barrel threads of the rotatable barrel engages the outer threads of the threaded sleeve, the rotatable barrel is seated closer to the threaded sleeve and, at block 2535, is fully seated the threaded sleeve. Fully seating the rotatable barrel to the threaded sleeve causes a top surface of the threaded sleeve to abut an interior surface of the rotatable barrel in instances where the detachable coupler is not within the internal mount. In some example embodiments, the threaded sleave does not full seat against the interior surface of the rotatable barrel due to the sloped surface of the threaded sleeve pushing the ball bearing set into the coupler detent before the threaded sleeve is fully seated with the rotatable barrel. This also causes the tactile ball bearing to be pressed downwards overcoming the biased spring force of the spring in the spring and ball channel. A tactile sensation is felt by the assembler of the prosthetic coupling device as the tactile ball bearing is pressed into and out of sequential interior barrel detents as described herein.

The method 2500 further includes, at block 2540, placing a retaining ring into a retaining slot formed on an interior surface of the rotatable barrel. The placement of the retaining ring and the formation of the retaining ring slot into the rotatable barrel may be based on the length of the internal mount such that the retaining ring slot is formed below the lowest end of the internal mount. The retaining ring, in an embodiment, prevents the rotatable barrel from being removable by a patient during operation. In the example embodiment shown in FIG. 3, for example, the counter-clockwise rotation of the rotatable barrel (e.g., when the patient is unlocking the detachable coupler from the internal mount) causes the rotatable barrel to move upwards. This movement of the rotatable barrel upwards causes the lowest portion of the internal mount to abut the retaining ring preventing the complete removal of the rotatable barrel from the prosthetic coupling device. Additionally, by preventing the removal of the rotatable barrel from the internal mount and threaded sleeve by the retaining ring, the spring and tactile ball bearing are kept in place.

The method 2500 also includes operatively coupling the detachable coupler in the internal mount. This process may be similar to what the patient engages in as the patient couples the lower pylon, foot, and detachable coupler to the remaining portions of the prosthetic coupling device including the internal mount and rotatable barrel as well as those other components described herein. As the detachable coupler is inserted into the internal mount, the ball bearing set may be moved radially away from the detachable coupler because the rotatable barrel has been placed in an unlocked position by the rotation of the rotatable barrel in a counter-clockwise direction in the embodiments described herein. This is because the sloped face of the threaded sleeve is not pressed against the ball bearing set and, instead, the ball bearing set is allowed to move a distance towards the ball bearing set barrier and away from a radial center of the internal mount. Once the detachable coupler is oriented properly via interaction of the registering post on the detachable coupler and the registering slot of the internal mount, the coupler detents are aligned with the horizontal ball bearing shafts that house the ball bearing sets.

The manufacturer or assembler of the prosthetic coupling device may then rotate the rotatable barrel in a clockwise direction to place the rotatable barrel in a locked position. As the rotatable barrel is rotated clockwise, the threaded sleeve is moved towards the rotatable barrel. This process causes the sloped surface of the threaded sleeve to push the ball bearing set through the horizontal ball bearing shaft and towards a terminal end of the horizontal ball bearing shaft closest to the center of the internal mount. The force provided by the sloped surface of the threaded sleeve causes a terminal ball bearing of the ball bearing set to extend out of a necked portion of the horizontal ball bearing shaft and engaging with the coupler detent. As this occurs, the detachable coupler is not locked into place with the internal mount.

Again, these mechanical functions resulting from the rotation of the rotatable barrel either clockwise or counter-clockwise by the patient allows the patient to disconnect the lower pylon, foot, and detachable coupler assembly from the remaining portions of the prosthetic device. In an example embodiment, the patient may own a first lower pylon and prosthetic foot that has a first type of shoe on the prosthetic foot such as a tennis shoe or sneaker. In this example embodiment, the patient may also own a second lower pylon and prosthetic foot combination that includes a dress shoe on the prosthetic foot. With the prosthetic coupling device, the patient may easily switch from the first lower pylon and prosthetic foot/shoe combination with the second lower pylon and prosthetic foot/shoe by rotating the rotatable barrel of the prosthetic coupling device in a first direction, removing the first lower pylon and prosthetic foot/shoe combination from the prosthetic coupling device, inserting the second lower pylon and prosthetic foot/shoe combination into the prosthetic coupling device, and turning the rotatable barrel in a second direction to lock the second lower pylon and prosthetic foot/shoe combination to the prosthetic coupling device and the upper portions of the prosthetic device. It is also clear that other, differently fitted, lower pylon and prosthetic foot combinations may be owned by the patient to quickly switch out different footwear when needed. Additionally, the prosthetic coupling device allows the patient to know when the lower pylon/prosthetic foot and securely locked to the prosthetic coupling device when a maximum rotation (e.g., a quarter turn rotation) of the rotatable barrel is completed. Additionally, the rotation of the rotatable barrel of the prosthetic coupling device includes tactile feedback so that the patient may feel that the rotatable barrel is rotating. This tactile feedback also allows the patient to confidently place weight on the prosthetic device knowing that the prosthetic coupling device has locked the detachable coupler into the internal mount. At this point, the method 2500 may end.

The blocks of the flow diagrams of FIG. 25 or steps and aspects of the operation of the embodiments herein and discussed above need not be performed in any given or specified order. It is contemplated that additional blocks, steps, or functions may be added, some blocks, steps or functions may not be performed, blocks, steps, or functions may occur contemporaneously, and blocks, steps, or functions from one flow diagram may be performed within another flow diagram.

Devices, modules, resources, or programs that are in communication with one another need not be in continuous communication with each other, unless expressly specified otherwise. In addition, devices, modules, resources, or programs that are in communication with one another can communicate directly or indirectly through one or more intermediaries.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A prosthetic coupling device comprising:
an internal mount including a shaft portion and a mounting portion;
a threaded sleeve formed around the mounting portion of the internal mount, the threaded sleeve including outer threads;
a rotatable barrel formed around the shaft portion and the mounting portion of the internal mount, the rotatable barrel including internal barrel threads that interface with the outer threads of the threaded sleeve;
a detachable coupler formed to fit within the mounting portion of the internal mount, the detachable coupler including a coupler detent formed on a radially external surface of the detachable coupler wherein a distal end of the detachable coupler is couplable to a prosthetic foot via a pylon;
and a horizontal ball bearing shaft formed through the internal mount, the horizontal ball bearing shaft housing a ball bearing set wherein the ball bearing set interfaces with the coupler detent to lock the detachable coupler to the internal mount when the outer threads of the threaded sleeve are fully seated into the internal barrel threads.

2. The prosthetic coupling device of claim 1 further comprising:
a spring and ball channel formed vertically into a top surface of the threaded sleeve to house a spring and tactile ball bearing.

3. The prosthetic coupling device of claim 2 further comprising:
a plurality of interior barrel detents formed on an interior surface of the rotatable barrel to engage with the tactile ball bearing to provide tactile feedback to a patient when the rotatable barrel is rotated by the patient.

4. The prosthetic coupling device of claim 1 further comprising:
a retaining ring slot formed in an interior surface of the rotatable barrel; and
a retaining ring formed into the retaining ring slot to prevent the rotatable barrel from being fully unscrewed from the internal mount and threaded sleeve.

5. The prosthetic coupling device of claim 1, wherein the ball bearing set disengages with the coupler detent to unlock the detachable coupler from the internal mount when the outer threads of the threaded sleeve are not fully seated into the internal barrel threads.

6. The prosthetic coupling device of claim 1 further comprising:
a registering slot formed into the internal mount to receive a registering pin formed on the detachable coupler to align the detachable coupler radially relative to the internal mount.

7. The prosthetic coupling device of claim 1 further comprising:
the threaded sleeve comprising a ball bearing channel to, during assembly of the prosthetic coupling device, conduct the ball bearing set into the horizontal ball bearing shaft; and
a ball bearing set barrier to, when the threaded sleeve is rotated around the internal mount, prevent the ball bearing set from exiting, radially, from the horizontal ball bearing shaft.

8. The prosthetic coupling device of claim 7 wherein a terminal end of the horizontal ball bearing shaft has an internal diameter smaller than a diameter of the ball bearing set to prevent the ball bearing set from exiting the ball bearing shaft at the terminal end.

9. A coupling device comprising:
an internal mount including a proximate shaft portion and a distal mounting portion;
a threaded sleeve formed around the distal mounting portion of the internal mount, the threaded sleeve including outer threads and secured to the internal mount via a fastening device to prevent the rotation of the threaded sleeve around the internal mount;
a rotatable barrel formed around the proximate shaft portion and the distal mounting portion of the internal mount, the rotatable barrel including internal barrel threads that interface with the outer threads of the threaded sleeve;
a detachable coupler formed to fit within the distal mounting portion of the internal mount, the detachable coupler including a coupler detent formed on a radially external surface of the detachable coupler wherein a distal end of the detachable coupler is couplable to a prosthetic foot via a pylon;
a horizontal ball bearing shaft formed through the internal mount, the horizontal ball bearing shaft housing a ball bearing set wherein the ball bearing set interfaces with the coupler detent to lock the detachable coupler to the internal mount when the outer threads of the threaded sleeve are fully seated into the internal barrel threads;
a retaining ring slot formed in an interior surface of the rotatable barrel;
and a retaining ring formed into the retaining ring slot to prevent the rotatable barrel from being fully unscrewed from the internal mount and threaded sleeve.

10. The coupling device of claim 9 further comprising:
a spring and ball channel formed vertically into a top surface of the threaded sleeve to house a spring and tactile ball bearing.

11. The coupling device of claim 10 further comprising:
a plurality of interior barrel detents formed on an interior surface of the rotatable barrel to engage with the tactile ball bearing to provide tactile feedback to a patient when the rotatable barrel is rotated by the patient.

12. The coupling device of claim 9 further comprising:
a retaining ring slot formed in an interior surface of the rotatable barrel; and
a retaining ring formed into the retaining ring slot to prevent the rotatable barrel from being fully unscrewed from the internal mount and threaded sleeve.

13. The coupling device of claim 12, wherein the placement of the retaining ring, the placement of the retaining ring slot, and a thickness of the retaining ring sets the rotational distance of the rotatable barrel.

14. The coupling device of claim 9 further comprising:

wherein the ball bearing set disengages with the coupler detent to unlock the detachable coupler from the internal mount when the outer threads of the threaded sleeve are not fully seated into the internal barrel threads.

15. The coupling device of claim 9 further comprising:

a registering slot formed in the internal mount to receive a registering pin formed on the detachable coupler to align the detachable coupler radially relative to the internal mount.

16. The of claim 15 further comprising:

wherein the ball bearing set disengages with the coupler detent to unlock the detachable coupler from the internal mount when the outer threads of the threaded sleeve are not fully seated into the internal barrel threads.

17. The prosthetic coupling device of claim 15 further comprising:

a registering slot formed in the internal mount to receive a registering pin formed on the detachable coupler to align the detachable coupler radially relative to the internal mount.

18. The prosthetic coupling device of claim 17 further comprising:

the threaded sleeve comprising a ball bearing channel to, during assembly of the prosthetic coupling device, conduct the ball bearing set into the horizontal ball bearing shaft; and a ball bearing set barrier to, when the threaded sleeve is rotated around the proximate shaft portion of the internal mount, prevent the ball bearing set from exiting, radially, from the horizontal ball bearing shaft.

19. A prosthetic coupling device comprising:

an internal mount including a proximate shaft portion and a distal mounting portion, the proximal shaft portion couplable to a socket of a prosthetic device;

a threaded sleeve formed around the distal mounting portion of the internal mount, the threaded sleeve including outer threads;

a rotatable barrel formed around the proximate shaft portion and the distal mounting portion of the internal mount, the rotatable barrel including internal barrel threads that interface with the outer threads of the threaded sleeve;

a detachable coupler formed to fit within the distal mounting portion of the internal mount, the detachable coupler including a coupler detent formed on a radially external surface of the detachable coupler, wherein a distal end of the detachable coupler is couplable to a prosthetic foot via a pylon;

a horizontal ball bearing shaft formed through the internal mount, the horizontal ball bearing shaft housing a ball bearing set wherein the ball bearing set interfaces with the coupler detent to lock the detachable coupler to the internal mount when the outer threads of the threaded sleeve are fully seated into the internal barrel threads;

a retaining ring slot formed in an interior surface of the rotatable barrel;

a retaining ring formed into the retaining ring slot to prevent the rotatable barrel from being fully unscrewed from the internal mount and threaded sleeve;

and a spring and ball channel formed vertically into a top surface of the threaded sleeve to house a spring and tactile ball bearing.

20. The prosthetic coupling device of claim 19, wherein a plurality of interior barrel detents formed on an interior surface of the rotatable barrel to engage with the tactile ball bearing to provide tactile feedback to a patient when the rotatable barrel is rotated by the patient.

* * * * *